United States Patent [19]
Schmitt et al.

[11] Patent Number: 4,588,433
[45] Date of Patent: May 13, 1986

[54] PHENOXYMETHANE DERIVATIVES FOR REGULATING PLANT GROWTH

[75] Inventors: Hans-Georg Schmitt, Leverkusen; Klaus Lürssen, Bergisch-Gladbach; Karlfried Wedemeyer, Cologne, all of Fed. Rep. of Germany

[73] Assignee: Bayer Aktiengesellschaft, Leverkusen, Fed. Rep. of Germany

[21] Appl. No.: 582,121

[22] Filed: Feb. 21, 1984

[30] Foreign Application Priority Data

Feb. 23, 1983 [DE] Fed. Rep. of Germany ....... 3306201
Dec. 7, 1983 [DE] Fed. Rep. of Germany ....... 3344235

[51] Int. Cl.$^4$ ............... C07C 149/40; C07C 147/107; A01N 31/14
[52] U.S. Cl. ........................................ 71/98; 71/103; 560/11; 560/12; 560/18; 562/429; 562/430; 562/432; 564/162; 564/54; 568/29; 568/30; 568/33; 568/36; 568/37; 568/44; 568/49; 568/52; 558/413; 558/415
[58] Field of Search ............ 71/98, 103; 560/11, 560/12, 18; 562/429, 430, 432; 260/465 D, 465 F; 564/162; 568/29, 30, 33, 36, 37, 44, 49, 54

[56] References Cited

U.S. PATENT DOCUMENTS 3,706,792 12/1972 Shen ..................... 560/11
3,983,164 9/1976 Thorne ................... 560/18
4,249,938 2/1981 Takemoto ................. 71/98
4,381,935 5/1983 Kosugo ................... 71/98

FOREIGN PATENT DOCUMENTS 0056319 7/1982 European Pat. Off. .
771064 3/1957 United Kingdom .

OTHER PUBLICATIONS

Chemische Bertichte, Band 111, Seiten 3497–3501, Verlag Chemie, Weinheim, DE; K. Schank et al.: "Synthese und Eigenschaften von Aryl–Arylsulfonylmethyl–Ethern" *Seite 3498*.
Synthetic Communications, Band 10, Nr. 12, 1980, Seiten 911–914, Marcel Dekker Inc., New York, USA; R. A. Holton et al.: "A New Protecting Group for Phenols: Phenylthiomethyl (PTM) Ethers".

Primary Examiner—Michael L. Shippen
Attorney, Agent, or Firm—Sprung Horn Kramer & Woods

[57] ABSTRACT

Phenoxymethane derivatives of the formula

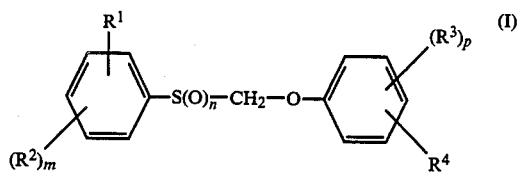

in which
R$^1$ represents hydrogen, alkyl, alkoxy, halogenoalkyl, halogenoalkoxy, halogen, alkoxycarbonyl, cycloalkoxycarbonyl or nitro,
R$^2$ represents hydrogen, alkyl or halogen,
R$^3$ represents hydrogen, alkyl, alkenyl, alkinyl, phenyl which is optionally substituted by alkyl and/or halogen, phenylalkyl which is optionally substituted by alkyl and/or halogen, alkoxy, phenoxy, halogenoalkyl, halogenoalkoxy, alkylthio, halogenoalkylthio, alkylsulphonyl, phenylthio, phenylsulphonyl, nitro or halogen,
R$^4$ represents hydrogen, alkyl, halogen, cycloalkoxycarbonyl, aminocarbonyl, alkylaminocarbonyl, dialkylaminocarbonyl, cycloalkylaminocarbonyl, di-cycloalkylaminocarbonyl, phenoxycarbonyl which is optionally substituted by halogen and/or alkyl, cyano or the radical of the formula —COOR,
wherein
R represents hydrogen, an alkali metal cation, one equivalent of an alkaline earth metal cation, alkyl, alkenyl, alkoxyalkyl, alkylthioalkyl or the radical of the formula —CH$_2$—O—(CH$_2$—CH$_2$—O)$_q$—Alk
wherein
Alk represents alkyl and
q represents 0, 1 or 2,
m represents 1, 2 or 3,
n represents 0, 1 or 2 and
p represents 1, 2 or 3,
are particularly suitable for regulating plant growth.

28 Claims, No Drawings

PHENOXYMETHANE DERIVATIVES FOR REGULATING PLANT GROWTH

The present invention relates to plant growth regulating compositions and to methods for regulating plant growth, using certain phenoxymethane derivatives. The invention also relates to certain new phenoxy-methane derivatives.

Some phenoxy-methane derivatives have already been described in the literature (compare Chem. Ber. 1978, 3497–3501). However, biological properties of these compounds are not yet known.

It has now been found that phenoxymethane derivatives of the formula

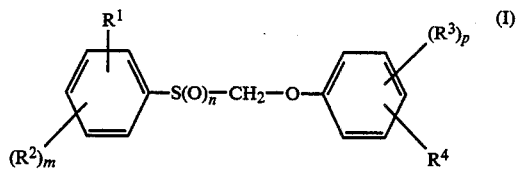

in which
R$^1$ represents hydrogen, alkyl, alkoxy, halogenoalkyl, halogenoalkoxy, halogen, alkoxycarbonyl, cycloalkoxycarbonyl or nitro,
R$^2$ represents hydrogen, alkyl or halogen,
R$^3$ represents hydrogen, alkyl, alkenyl, alkinyl, phenyl which is optionally substituted by alkyl and/or halogen, phenylalkyl which is optionally substituted by alkyl and/or halogen, alkoxy, phenoxy, halogenoalkyl, halogenoalkoxy, alkylthio, halogenoalkylthio, alkylsulfonyl, phenylthio, phenylsulphonyl, nitro or halogen,
R$^4$ represents hydrogen, alkyl, halogen, cycloalkoxycarbonyl, aminocarbonyl, alkylaminocarbonyl, dialkylaminocarbonyl, cycloalkylaminocarbonyl, di-cycloalkylaminocarbonyl, phenoxycarbonyl which is optionally substituted by halogen and/or alkyl, cyano or the radical of the formula —COOR,
wherein
R represents hydrogen, an alkali metal cation, one equivalent of an alkaline earth metal cation, alkyl, alkenyl, alkoxyalkyl, alkylthioalkyl or the radical of the formula
—CH$_2$—O—(CH$_2$—CH$_2$—O)$_q$—Alk
wherein
Alk represents alkyl and
q represents 0, 1 or 2,
m represents 1, 2 or 3,
n represents 0, 1 or 2 and
p represents 1, 2 or 3,
are particularly suitable for regulating plant growth.

Accordingly, the present invention provides a plant growth-regulating composition containing as active ingredient a compound of the formula (I) in admixture with a solid or liquefied gaseous diluent or carrier or in admixture with a liquid diluent or carrier containing a surface-active agent.

The invention also provides a method of regulating the growth of plants which comprises applying to the plants, or to a habitat thereof, a compound of the formula (I) alone or in the form of a composition containing as active ingredient a compound of the present invention in admixture with a diluent or carrier.

Formula (I) provides a general definition of the substances which can be used according to the invention. In this formula, R$^1$ preferably represents hydrogen, straight-chain or branched alkyl with 1 to 6 carbon atoms, straight-chain or branched halogenoalkyl with 1 to 6 carbon atoms and 1 to 5 halogen atoms, straight-chain or branched alkoxy with 1 to 6 carbon atoms, halogenoalkoxy with 1 to 6 carbon atoms and 1 to 5 halogen atoms, alkoxycarbonyl with 1 to 10 carbon atoms in the alkoxy group, cycloalkoxycarbonyl with 3 to 8 carbon atoms in the cycloalkyl group, fluorine, chlorine, bromine, iodine or nitro. R$^2$ preferably represents hydrogen, straight-chain or branched alkyl with 1 to 6 carbon atoms, fluorine, chlorine, bromine or iodine. R$^3$ preferably represents hydrogen, straight-chain or branched alkyl with 1 to 6 carbon atoms, straight-chain or branched alkenyl with 3 to 6 carbon atoms, straight-chain or branched alkinyl with 3 to 6 carbon atoms, phenyl which is optionally substituted by alkyl with 1 to 4 carbon atoms, fluorine, chlorine, bromine and/or iodine, benzyl which is optionally substituted by alkyl with 1 to 4 carbon atoms, fluorine, chlorine, bromine and/or iodine, alkoxy with 1 to 6 carbon atoms, phenoxy, halogenoalkyl with 1 to 6 carbon atoms and 1 to 5 halogen atoms, halogenoalkoxy with 1 to 6 carbon atoms and 1 to 5 halogen atoms, alkylthio with 1 to 6 carbon atoms, halogenoalkylthio with 1 to 6 carbon atoms and 1 to 5 halogen atoms, alkylsulphonyl with 1 to 6 carbon atoms, phenylthio, phenylsulphonyl, nitro, fluorine, chlorine, bromine or iodine. R$^4$ preferably represents hydrogen, straight-chain or branched alkyl with 1 to 6 carbon atoms, fluorine, chlorine, bromine, iodine, cycloalkoxycarbonyl with up to 10 carbon atoms in the cycloalkyl group, aminocarbonyl, alkylaminocarbonyl with 1 to 6 carbon atoms in the alkyl group, dialkylaminocarbonyl with 1 to 6 carbon atoms in each alkyl group, cycloalkylaminocarbonyl with 3 to 8 carbon atoms in the cycloalkyl group, di-cycloalkylaminocarbonyl with 3 to 8 carbon atoms in each cycloalkyl group, phenoxycarbonyl which is optionally substituted by alkyl with 1 to 4 carbon atoms, fluorine, chlorine, bromine and/or iodine, cyano or the radical of the formula —COOR, in which R preferably represents hydrogen, a sodium or potassium cation, one equivalent of a magnesium or calcium cation, alkyl with 1 to 10 carbon atoms, alkenyl with 2 to 10 carbon atoms, alkoxyalkyl with 1 to 6 carbon atoms in the alkoxy group and 1 to 6 carbon atoms in the alkyl part, alkylthioalkyl with 1 to 6 carbon atoms in the alkylthio group and 1 to 6 carbon atoms in the alkyl part, or the radical of the formula —CH$_2$—O—(CH$_2$—CH$_2$—O)$_q$-Alk, in which Alk preferably represents alkyl with 1 to 6 carbon atoms and q represents 0, 1 or 2. The index m preferably represents 1 or 2, the index n represents 0, 1 or 2 and the index p preferably represents 1 or 2.

Very particularly preferred substances are those of the formula (I)
in which
R$^1$ represents hydrogen, straight-chain or branched alkyl with 1 to 4 carbon atoms, straight-chain or branched alkoxy with 1 to 4 carbon atoms, halogenoalkoxy with 1 to 3 carbon atoms and 1 to 5 fluorine, chlorine and/or bromine atoms, halogenoalkyl with 1 to 3 carbon atoms and 1 to 5 fluorine, chlorine and/or bromine atoms, alkoxycarbonyl with 1 to 4 carbon atoms in the alkoxy group, cycloalkoxycarbonyl with 3 to 6 carbon atoms in the cycloalkyl group, fluorine, chlorine, bromine or nitro, R² represents hydrogen, straight-chain or branched alkyl with 1 to 4 carbon atoms, fluorine, chlorine or bromine, R³ represents hydrogen, straight-chain or branched alkyl with 1 to 4 carbon atoms, straight-chain or branched alkenyl with 3 to 5 carbon atoms, straight-chain or branched alkinyl with 3 to 5 carbon atoms, phenyl which is optionally substituted by alkyl with 1 to 3 carbon atoms, fluorine, chlorine and/or bromine, benzyl which is optionally substituted by alkyl with 1 to 3 carbon atoms, fluorine, chlorine and/or bromine, alkoxy with 1 to 4 carbon atoms, phenoxy, halogenoalkyl with 1 to 3 carbon atoms and 1 to 5 fluorine, chlorine and/or bromine atoms, halogenoalkoxy with 1 to 3 carbon atoms and 1 to 5 fluorine, chlorine and/or bromine atoms, alkylthio with 1 to 4 carbon atoms, halogenoalkylthio with 1 to 3 carbon atoms and 1 to 5 fluorine, chlorine and/or bromine atoms, alkylsulphonyl with 1 to 4 carbon atoms, phenylthio, phenylsulphonyl, nitro, fluorine, chlorine or bromine, R⁴ represents hydrogen, straight-chain or branched alkyl with 1 to 4 carbon atoms, fluorine, chlorine, bromine, cycloalkoxycarbonyl with 3 to 8 carbon atoms in the cycloalkyl group, aminocarbonyl, alkylaminocarbonyl with 1 to 4 carbon atoms in the alkyl group, dialkylaminocarbonyl with 1 to 4 carbon atoms in each alkyl group, cycloalkylaminocarbonyl with 3 to 7 carbon atoms in the cycloalkyl group, dicycloalkyl-aminocarbonyl with 3 to 7 carbon atoms in each cycloalkyl group, phenoxycarbony which is optionally substituted by alkyl with 1 to 3 carbon atoms, fluorine, chlorine and/or bromine, cyano or the radical of the formula —COOR, wherein
R represents hydrogen, a sodium or potassium cation, one equivalent of a magnesium or calcium cation, alkyl with 1 to 8 carbon atoms, alkenyl with 2 to 8 carbon atoms, alkoxyalkyl with 1 to 4 carbon atoms in the alkoxy group and 1 to 4 carbon atoms in the alkyl part, alkylthioalkyl with 1 to 4 carbon atoms in the alkylthio group and 1 to 4 carbon atoms in the alkyl part or the radical of the formula —CH₂—O—(CH₂—CH₂—O)$_q$-Alk, wherein
Alk represents alkyl with 1 to 4 carbon atoms and
q represents 0, 1 or 2,
m represents 1 or 2,
n represents 0, 1 or 2 and
p represents 1 or 2.

A particularly preferred group of compounds which can be used according to the invention comprises the substances of the formula

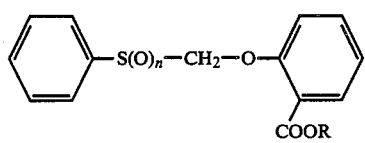

(Ia)

in which
n represents 0, 1 or 2,
R represents hydrogen, a sodium or potassium cation, one equivalent of a magnesium or calcium cation, alkyl with 1 to 8 carbon atoms, alkenyl with 2 to 8 carbon atoms, alkoxyalkyl with 1 to 4 carbon atoms in the alkoxy group and 1 to 4 carbon atoms in the alkyl part, alkylthioalkyl with 1 to 4 carbon atoms in the alkylthio group and 1 to 4 carbon atoms in the alkyl part, or the radical of the formula —CH₂—O—(CH₂—CH₂—O)$_q$-Alk, wherein
Alk represents alkyl with 1 to 4 carbon atoms and
q represents 0, 1 or 2.

Examples which may be mentioned of phenoxymethane-derivatives of the formula (I) which can be used according to the invention are: 1-phenoxy-1-phenylthio-methane, 1-phenoxy-1-phenylsulphinyl-methane, 1-phenoxy-1-phenylsulphonyl-methane, 1-(4,6-dibromo-2-methoxycarbonylphenoxy)-1-phenylthio-methane, 1-(5-chloro-2-methoxycarbonyl-phenoxy)-1-phenylthio-methane, 1-(4-bromo-2-ethoxycarbonyl-phenoxy)-1-phenylthio-methane, 1-(2-ethoxycarbonyl-4-fluoro-phenoxy)-1-phenylthio-methane, 1-(6-methoxy-2-methoxycarbonyl-phenoxy)-1-phenylthiomethane, 1-(4-trifluoromethyl-phenoxy)-1-phenylsulphonylmethane, 1-[2-(3-methyl-phenyl)-oxycarbonyl-phenoxy]-1-phenylthio-methane, 1-[2-(4-chlorophenyl)-oxycarbonylphenoxy]-1-phenylthio-methane, 1-(3-phenoxy-phenoxy)-1-phenylthio-methane, 1-(3-trifluoromethoxy-phenoxy)-1-phenylthio-methane, 1-(4-trifluoromethylthio-phenoxy)-1-phenylthio-methane, 1-(2-chloro-4-trifluoromethylphenoxy)-1-phenylthio-methane, 1-(2-isopropoxycarbonyl-6-nitro-phenoxy)-1-phenylthio-methane, 1-(2-propoxycarbonyl-4-nitro-phenoxy)-1-phenylthio-methane, 1-(2-ethoxycarbonyl-4,6-dinitro-phenoxy)-1-phenylthio-methane, 1-(2-methoxy-6-methyl-phenoxy)-1-phenylthio-methane, 1-(4-chloro-2-ethoxycarbonyl-6-methyl)-1-phenylthio-methane, 1-(2-methoxycarbonyl-4-methyl-phenoxy)-1-phenylthiomethane, 1-(2-ethoxycarbonyl-5-methyl-phenoxy)-1-phenylthio-methane, 1-(2-ethoxycarbonyl-4-tert.-butyl-phenoxy)-1-phenylthio-methane, 1-(2-methoxycarbonyl-phenoxy)-1-phenylthio-methane, 1-(2-methoxycarbonyl-phenoxy)-1-phenylsulphinyl-methane, 1-(2-methoxycarbonyl-phenoxy)-1-phenylsulphonyl-methane, 1-(2-methoxycarbonyl-6-trifluoromethoxy-phenoxy)-1-phenylthio-methane, 1-(2-methoxycarbonyl-4-trifluoromethyl-phenoxy)-1-phenylthio-methane, 1-(2-ethoxycarbonyl-phenoxy)-1-phenylthio-methane, 1-(2-ethoxycarbonyl-phenoxy)-1-phenylsulphinyl-methane, 1-(2-ethoxycarbonyl-phenoxy)-1-phenylsulphonyl-methane, 1-(2-methoxycarbonyl-phenoxy)-1-(2-trifluoromethylphenylthio)-methane, 1-(2-methoxycarbonyl-phenoxy)-1-(2-nitro-phenylthio)-methane, 1-(2-ethoxycarbonyl-phenoxy)-1-(2-nitro-phenylthio)-methane, 1-(2-methoxycarbonyl-phenoxy)-1-(2,3-dimethyl-phenylthio)-methane, 1-(2-propoxycarbonylphenoxy)-1-phenylthio-methane, 1-(2-propoxycarbonylphenoxy)-1-phenylsulphinyl-methane, 1-(2-propoxycarbonylphenoxy)-1-phenylsulphonyl-methane, 1-(2-isopropoxycarbonyl-phenoxy)-1-phenylthio-methane, 1-(2-isopropoxycarbonyl-phenoxy)-1-phenylsulphinyl-methane, 1-(2-isopropoxycarbonyl-phenoxy)-1-phenylsulphonyl-methane, 1-(2-butoxycarbonyl-phenoxy)-1-phenylthio-methane, 1-(2-butoxycarbonyl-phenoxy)-1-phenylsulphinyl-methane, 1-(2-butoxycarbonyl-phenoxy)-1-phenylsulphonyl-methane, 1-(2-isobutoxycarbonyl-phenoxy)-1-phenylthio-methane, 1-(2-sec.-butoxycarbonyl-phenoxy)-1-phenylthio-methane, 1-(2-pentoxycarbonyl-phenoxy)-1-phenylthio-methane, 1-(2-hexoxycarbonyl-phenoxy)-1- phenylthio-methane, 1-(2-heptoxycarbonyl-phenoxy)-1-phenylthio-methane, 1-(2-octyloxycarbonyl-phenoxy-1-phenylthio-methane, 1-(2-cyclohexoxycarbonyl-phenoxy-1-phenylthio-methane, 1-phenoxy-1-(4-chlorophenylthio)-methane, 1-phenoxy-1-(4-tolylthio)-methane, 1-(2-phenylphenoxy)-1-(4-chlorophenylthio)-methane, 1-phenoxy-1-(4-chlorophenylsulphonyl)-methane, 1-phenoxy-1-(4-tolylsulphonyl)-methane, 1-(2-phenylphenoxy)-1-(4-chlorophenylsulphonyl)-methane, 1-(4-chloro-3-methyl-phenoxy)-1-(4-chlorophenylthio)-methane, 1-(4-chloro-3-methyl-phenoxy)-1-(4-tolylthio)-methane, 1-(4-chloro-3-methyl-phenoxy)-1-phenylthio-methane, 1-(4-chloro-phenoxy)-1-(4-chlorophenylthio)-methane, 1-(4-chlorophenoxy)-1-(4-chlorophenylsulphinyl)-methane, 1-(4-chloro-phenoxy)-1-(4-chlorophenylsulphonyl)-methane, 1-(4-chlorophenoxy)-1-(4-tolylthio)-methane, 1-(4-chlorophenoxy)-1-phenylthio-methane, 1-(4-chloro-3-methylphenoxy)-1-(4-chlorophenylsulphonyl)-methane, 1-(4-chloro-3-methyl-phenoxy)-1-(4-tolylsulphonyl)-methane, 1-(4-chloro-3-methyl-phenoxy)-1-phenylsulphinyl-methane, 1-(4-chloro-phenoxy)-1-(4-tolylsulphonyl)-methane, 1-(4-chloro-pheoxy)-1-phenylsulphonyl-methane, 1-(2-phenylphenozy)-1-phenylthio-methane, 1-(2-phenyl-pheoxy)-1-(4-tolylthio)-methane, 1-(2-phenyl-phenoxy)-1-phenylsulphonyl-methane, 1-(2-phenyl-phenoxy)-1-(4-tolylsulphonyl)-methane, 1-phenoxy-1-(4-tert.-butyl-phenylthio)-methane, 1-(4-chlorophenoxy)-1-(4-tert.-butyl-phenylthio)-methane, 1-phenoxy-1-(4-tert.-butyl-phenylsulphonyl)-methane, 1-(4-chloro-3-methyl-phenoxy)-1-(4-tert.-butyl-phenylsulphinyl-methane, 1-(2-isopropoxy-phenoxy)-1-(4-chlorophenylthio)-methane, 1-(2-methoxycarbonyl-phenoxy)-1-(4-chlorophenylthio)-methane, 1-(3-methyl-phenoxy)-1-(4-chloro-phenylthio)-methane, 1-(2,4-dichloro-phenoxy)-1-(4-tolylthio)-methane, 1-(2-isopropoxy-phenoxy)-1-(4-tolylthio)-methane, 1-(2-methoxycarbonyl-phenoxy)-1-(4-chloro-phenulsulphonyl)-methane, 1-(2-isopropoxy-phenoxy)-1-(4-chlorophenylsulphonyl)-methane, 1-(3-methyl-phenoxy)-1-(4-tolylsulphonyl)-methane, 1-(2,4-dichloro-phenoxy) 1-(4-tolylsulphonyl)-methane, 1-(2-methoxycarbonylphenoxy)-1-(4-tolylthio)-methane, 1-(3-methoxy-phenoxy)-1-(4-chlorophenylthio)-methane, 1-(2-methoxycarbonyl-phenoxy)-1-84-tolylsulphonyl)-methane, 1-(2-methoxycarbonyl-phenoxy)-1-phenylsulphonyl-methane, 1-(2,4-dichloro-phenoxy)-1-(2-methoxycarbonyl-phenylthio)-methane, 1-(2,4-dichloro-phenoxy)-1-(2-methoxycarbonyl-phenylsulphinyl)-methane, 1-(2,4-dichloro-ycarbonyl-phenoxy)-1-(2-methoxycarbonyl-phenylsulphonyl)-methane, 1-(2-methoxycarbonylphenoxy)-1-(3,4-dichloro-phenylthio)-methane, 1-(2-methoxycarbonyl-phenoxy)-1-(2,5-dichloro-phenylthio)methane, 1-(2-methoxycarbonyl-phenoxy)-1-(4-tert.-butylphenylthio)-methane, 1-[2-(3-methyl-butyl)oxycarbonylphenoxy]-1-phenylthio-methane, 1-(2-phenoxycarbonylphenoxy)-1-(phenylthio)-methane, 1-(2-aminocarbonylphenoxy)-1-phenylthio-methane, 1-(3-methoxycarbonylphenoxy)-1-phenylthio-methane, 1-(3-methoxycarbonylphenoxy)-1-pheylsulphinyl-methane, 1-(3-methoxy-carbonyl-phenoxy)-1-phenylsulphonyl-methane, 1-(4-ethoxycarbonylphenoxy)-1-phenylthio-methane, 1-(4-propoxycarbonylphenoxy)-1-phenylthio-methane, 1-(2-cyano-4-nitrophenoxy)-1-phenylthio-methane, 1-(4-cyano-phenoxy)-1-phenylthio-methane, 1-(2,6-dibromo-4-cyano-phenoxy)-1-phenylthio-methane, 1-(2,6-dibromo-4-cyano-phenoxy)-1-phenylsulphinyl-methane and 1-(2,6-dibromo-4-cyanophenoxy)-1-phenylsulphonyl-methane.

Some of the phenoxymethane derivatives which can be used according to the invention are known (compare Chem. Ber. 1978, 3497–3501).

Some of the phenoxymethane derivatives, which can be used according to the invention, are not yet known.

Thus, the invention provides, as new compounds, the phenoxymethane derivatives of the formula

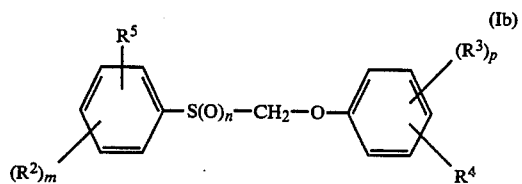

in which
R$^5$ represents alkyl with more than one carbon atoms, alkoxy, halogenoalkyl, halogenoalkoxy, fluorine, bromine, iodine, alkoxycarbonyl, cycloalkoxycarbonyl, or nitro,
R$^2$ represents hydrogen, alkyl or halogen,
R$^3$ represents hydrogen, alkyl, alkenyl, alkinyl, phenyl which is optionally substituted by alkyl and/or halogen, phenylalkyl which is optionally substituted by alkyl and/or halogen, alkoxy, phenoxy, halogenoalkyl, halogenoalkoxy, alkylthio, halogenoalkylthio, alkylsulphonyl, phenylthio, phenylsulphonyl, nitro or halogen,
R$^4$ represents hydrogen, alkyl, halogen, alkoxycarbonyl, cycloalkoxycarbonyl, aminocarbonyl, alkylaminocarbonyl, dialkylaminocarbonyl, cycloalkylaminocarbonyl, di-cycloalkyl-aminocarbonyl, phenoxycarbonyl which is optionally substituted by halogen and/or alkyl or cyano,
m represents 1, 2 or 3,
n represents 0, 1 or 2 and
p represents 1, 2 or 3, and
R$^5$ also represents hydrogen or chlorine as long as R$^3$ does not represent hydrogen, chlorine, methyl or nitro.

The phenoxy-methane derivatives of the formula (Ib) can be prepared in a simple manner by several processes. Thus, phenoxy-methane derivatives of the formula (Ib) are obtained by a process in which
(a) thiophenol derivatives of the formula

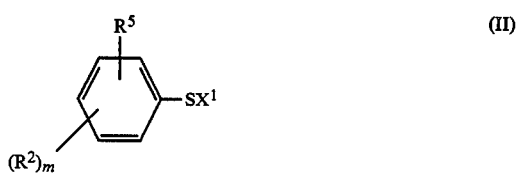

in which
R$^2$, R$^5$ and m have the abovementioned meaning and
X$^1$ represents hydrogen or an alkali metal atom, are reacted with halogenomethyl phenyl ethers of the formula

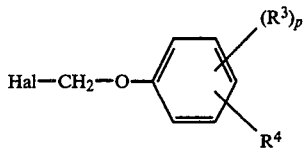 (III)

in which
R³, R⁴ and p have the abovementioned meaning and
Hal represents chlorine, bromine or iodine, if appropriate in the presence of an acid acceptor and if appropriate in the presence of a diluent, and, if appropriate, the phenoxy-methane derivatives thereby formed, of the formula

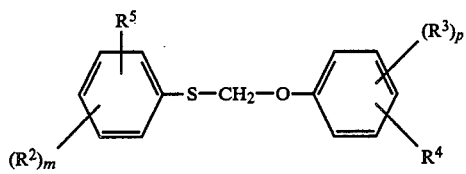 (Ic)

in which
R², R³, R⁴, R⁵, m and p have the abovementioned meaning,
are then reacted with an oxidising agent, if appropriate in the presence of a diluent, or (b) phenol derivatives of the formula

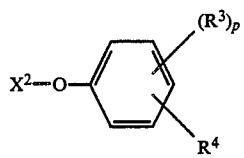 (IV)

in which
R³, R⁴ and p have the abovementioned meaning and
X² represents hydrogen or an alkali metal atom, are reacted with halogenomethyl phenyl sulphides of the formula

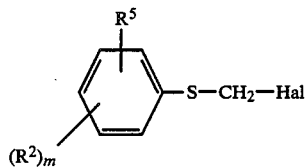 (V)

in which
R², R⁵ and m have the abovementioned meaning and
Hal represents chlorine, bromine or iodine,
if appropriate in the presence of an acid acceptor and if appropriate in the presence of a diluent, and, if appropriate, the phenoxy-methane derivatives thereby formed, of the formula

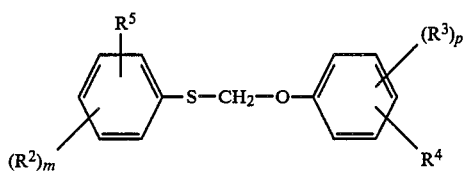 (Ic)

in which
R², R³, R⁴, R⁵, m and p have the abovementioned meaning,
are then reacted with an oxidising agent, if appropriate in the presence of a diluent, or (c) sulphinic acid salts of the formula

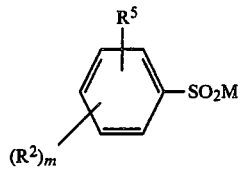 (VI)

in which
R², R⁵ and m have the abovementioned meaning and
M represents an alkali metal atom,
are reacted with halogenomethyl phenyl ethers of the formula

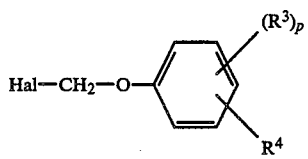 (III)

in which
R³, R⁴ and p have the abovementioned meaning and
Hal represents chlorine, bromine or iodine,
if appropriate in the presence of a catalyst and if appropriate in the presence of a diluent.

The invention also provides, as new compounds, the phenoxymethane derivatives of the formula

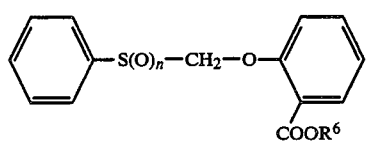 (Id)

in which
n represents 0, 1 or 2 and
R⁶ represents hydrogen, an alkali metal cation, one equivalent of an alkaline earth metal cation, alkyl with more than 1 carbon atom, alkenyl, alkoxyalkyl, alkylthioalkyl or the radical of the formula
—CH₂—O—(CH₂—CH₂—O)$_q$-Alk
wherein
Alk represents alkyl and
q represents 0, 1 or 2.

The phenoxy-methane derivatives of the formula (Id) can be prepared by a process in which (d) compounds of the formula

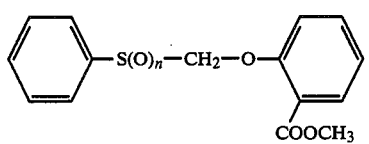 (Ie)

in which
n has the abovementioned meaning,
either
(α) are reacted with compounds of the formula

R⁷OH    (VII)

in which
R⁷ represents alkyl with more than one carbon atom, alkenyl, alkoxyalkyl, alkylthioalkyl or the radical of the formula —CH₂—O—(CH₂—CH₂—O)-$_q$—Alk,
wherein
Alk represents alkyl and
q represents 0, 1 or 2,
in the presence of a base and, if appropriate, in the presence of a diluent, or
(β) are reacted with bases of the formula

M¹OH    (VIII)

in which
M¹ represents an alkali metal cation or one equivalent of an alkaline earth metal cation,
in the presence of a diluent, and the products are then acidified with a strong acid and, if appropriate, subsequently reacted again with a base of the formula

M¹OH    (VIII)

in which
M¹ has the abovementioned meaning,
in the presence of a diluent.

Those substances of the formula (I) which are not described by the formulae (Ib) and (Id) can also be prepared by the abovementioned processes.

Particularly preferred compounds of the formula (Ib) are those substances
in which
R⁵ represents straight-chain or branched alkyl with 2 to 4 carbon atoms, straight-chain or branched alkoxy with 1 to 4 carbon atoms, halogenoalkyl with 1 to 3 carbon atoms and 1 to 5 fluorine, chlorine and/or bromine atoms, halogenoalkoxy with 1 to 3 carbon atoms and 1 to 5 fluorine, chlorine and/or bromine atoms, alkoxycarbonyl with 1 to 4 carbon atoms in the alkoxy group, cycloalkoxycarbonyl with 3 to 6 carbon atoms in the cycloalkyl group, fluorine, bromine or nitro,
R² represents hydrogen, straight-chain or branched alkyl with 1 to 4 carbon atoms, fluorine, chlorine or bromine,
R³ represents hydrogen, straight-chain or branched alkyl with 1 to 4 carbon atoms, straight-chain or branched alkenyl with 3 to 5 carbon atoms, straight-chain or branched alkinyl with 3 to 5 carbon atoms, phenyl which is optionally substituted by alkyl with 1 to 3 carbon atoms, fluorine, chlorine and/or bromine, benzyl which is optionally substituted by alkyl with 1 to 3 carbon atoms, fluorine, chlorine and/or bromine, alkoxy with 1 to 4 carbon atoms, phenoxy, halogenoalkyl with 1 to 3 carbon atoms and 1 to 5 fluorine, chlorine and/or bromine atoms, halogenoalkoxy with 1 to 3 carbon atoms and 1 to 5 fluorine, chlorine and/or bromine atoms, alkylthio with 1 to 4 carbon atoms, halogenoalkylthio with 1 to 3 carbon atoms and 1 to 5 fluorine, chlorine and/or bromine atoms, alkylsulphonyl with 1 to 4 carbon atoms, phenylthio, phenylsulphonyl, nitro, fluorine, chlorine or bromine,
R⁴ represents hydrogen, straight-chain or branched alkyl with 1 to 4 carbon atoms, fluorine, chlorine, bromine, alkoxycarbonyl with 1 to 8 carbon atoms in the alkoxy group, cycloalkoxycarbonyl with 3 to 8 carbon atoms in the cycloalkyl group, aminocarbonyl, alkylaminocarbonyl with 1 to 4 carbon atoms in the alkyl group, dialkylaminocarbonyl with 1 to 4 carbon atoms in each alkyl group, cycloalkylaminocarbonyl with 3 to 7 carbon atoms in the cycloalkyl group, dicycloalkyl-aminocarbonyl with 3 to 7 carbon atoms in each cycloalkyl group, phenoxycarbonyl which is optionally substituted by alkyl with 1 to 3 carbon atoms, fluorine, chlorine and/or bromine or cyano,
m represents 1 or 2,
n represents 0, 1 or 2 and
p represents 1 or 2, and
R⁵ additionally also represents hydrogen or chlorine, as long as R³ does not represent hydrogen, methyl or nitro.

Particularly preferred compounds of the formula (Id) are those substances
in which
n represents 0, 1 or 2 and
R⁶ represents hydrogen, a sodium or potassium cation, one equivalent of a magnesium or calcium cation, alkyl with 2 to 8 carbon atoms, alkenyl with 2 to 8 carbon atoms, alkoxyalkyl with 1 to 4 carbon atoms in the alkoxy group and 1 to 4 carbon atoms in the alkyl part, alkylthioalkyl with 1 to 4 carbon atoms in the alkylthio group and 1 to 4 carbon atoms in the alkyl part or the radical of the formula —CH₂—O—(CH₂—CH₂—O)$_q$—Alk,
wherein
Alk represents alkyl with 1 to 4 carbon atoms and
q represents 0, 1 or 2.

If methyl 2-mercapto-benzoate and chloromethyl 2,4-dichloro-phenyl ether are used as starting substances, the course of process (a) according to the invention can be represented by the following equation:

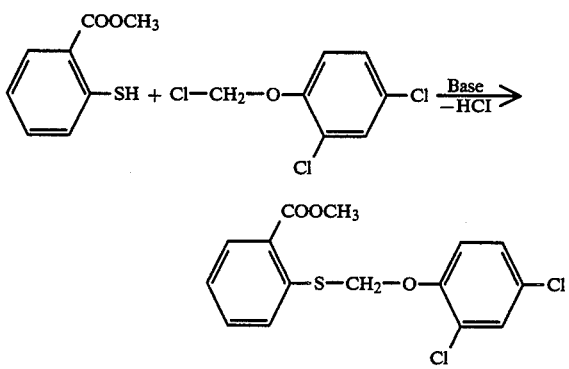

If sodium phenolate and chloromethyl 4-methoxyphenyl sulphide are used as starting substances, the course of process (b) according to the invention can be represented by the following equation:

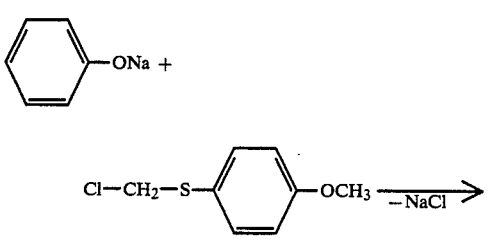

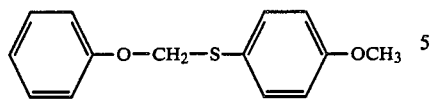

If sodium (4-chloro-benzene)-sulphinate and chloromethyl 4-ethyl-phenyl ether are used as starting substances, the course of process (c) according to the invention can be represented by the following equation:

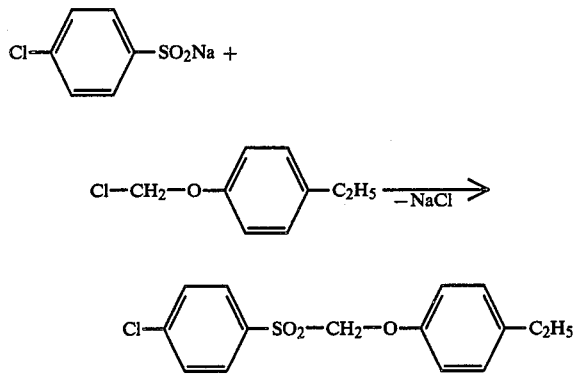

If methyl 2-(phenylthio-methoxy)-benzoate and n-octanol are used as starting substances, the course of process (d, variant α) according to the invention can be represented by the following equation:

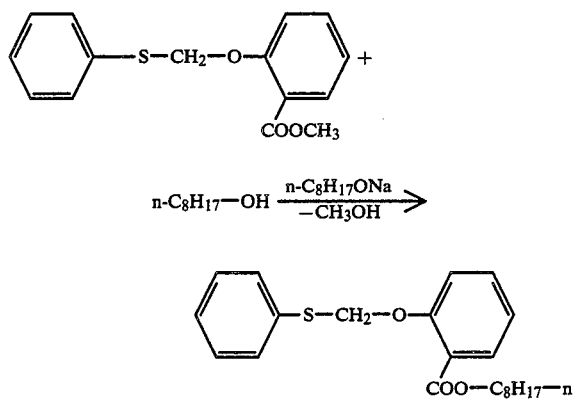

If methyl 2-(phenylthio-methoxy)-benzoate is used as the starting substance, potassium hydroxide is used as the base and hydrochloric acid is used for acidification, the course of process (d, variant β) according to the invention can be represented by the following equation:

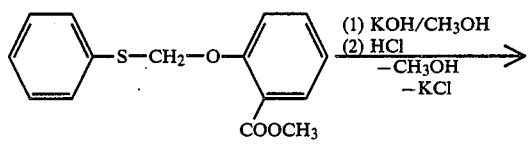

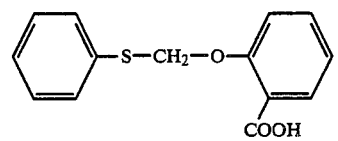

The formula (II) provides a general definition of the thiophenol derivatives required as starting substances in process (a) according to the invention. In this formula, $R^2$, $R^5$ and m preferably have those meanings which have already been mentioned as particularly preferred for these radicals and for this index in connection with the description of the compounds of the formula (Io). $X^1$ preferably represents hydrogen, sodium or potassium.

The thiophenol derivatives of the formula (II) are known, or they can be prepared in a simple manner by known processes (compare Houben-Weyl "Methoden der Organischen Chemie" ("Methods of Organic Chemistry"), Volume IX, Thieme-Verlag, Stuttgart 1955).

Formula (III) provides a general definition of the halogenomethyl phenyl ethers also required as starting substances in process (a) according to the invention. In this formula, $R^3$, $R^4$ and p preferably have those meanings which have already been mentioned as particularly preferred for these radicals and for this index in connection with the description of the compounds of the formula (Ib). Hal preferably represents chlorine or bromine.

The halogenomethyl phenyl ethers of the formula (III) are known, or they can be prepared in a simple manner by known methods (compare J. Appl. Chem. 3 (1953), 253-263).

Acid acceptors which can be used in carrying out process (a) according to the invention are all the acid-binding agents usually suitable for such reactions. Preferred acid acceptors are alkali metal carbonates and alkaline earth metal carbonates, such as sodium carbonate, potassium carbonate, magnesium carbonate and calcium carbonate, and furthermore alkali metal alcoholates, such as sodium methylate or ethylate and potassium methylate or ethylate, as well as aliphatic, aromatic or heterocyclic amines, for example triethylamine, trimethylamine, dimethylaniline, dimethylbenzyl-amine, 1,5-diazobicyclo[4.3.0]non-5-ene (DBN), 1,8-diazabicyclo[5.4.0]undec-7-ene (DBU) and pyridine.

Possible diluents in carrying out process (a) according to the invention are virtually all the inert organic solvents. Solvents which can preferably be used are aliphatic and aromatic, optionally halogenated hydrocarbons, such as pentane, hexane, heptane, cyclohexane; petroleum ether, benzine, ligroin, benzene, toluene, xylene, methylene chloride, ethylene chloride, chloroform, carbon tetrachloride, chlorobenzene and o-dichlorobenzene, ethers, such as diethyl ether and dibutyl ether, glycol dimethyl ether and diglycol dimethyl ether, tetrahydrofuran and dioxane, alcohols, such as methanol and ethanol, and furthermore esters, such as methyl acetate and ethyl acetate, nitriles, such as, for example, acetonitrile and propionitrile, amides, such as, for example, dimethylformamide, dimethylacetamide and N-methylpyrrolidone, and dimethylsulphoxide, tetramethylenesulphone and hexamethylphosphoric acid triamide.

The reaction temperatures can be varied within a substantial range in process (a) according to the invention. In general, the reaction is carried out at temperatures between 0° C. and 100° C., preferably between 20° C. and 80° C.

Process (a) according to the invention is in general carried out under normal pressure. However, it is also possible to carry out the process under increased or reduced pressure.

For carrying out process (b) according to the invention, the starting substances of the formulae (II) and (III) are in general employed in approximately equimolar amounts. However, it is also possible to use one of the two components in a larger excess. The reactions are in general carried out in a suitable diluent, if appropriate in the presence of an acid-binding agent, and the reaction mixture is subsequently stirred at the particular temperature required, until the reaction has ended. Working up is in each case effected by customary methods.

For the preparation of those compounds of the formula (Ib) in which n represents 1 or 2, the phenoxymethane derivatives of the formula (Ic) initially formed in process (a) according to the invention are reacted with an oxidising agent, if appropriate in the presence of a diluent.

Oxidising agents which can be used are all the customary oxygen-donating oxidising agents which are capable of converting sulphides into sulphoxides or into sulphones. Oxidising agents which can preferably be used are hydrogen peroxide, peracetic acid and m-chloroperbenzoic acid.

Possible diluents in carrying out this oxidation are all the organic solvents which can customarily be used for such oxidations. Solvents which can preferably be used are alcohols, such as methanol or ethanol, and furthermore carboxylic acids, such as formic acid and acetic acid. It is also possible to use water, if appropriate mixed with one of the organic solvents mentioned. The oxidation with m-chloroperbenzoic acid is preferably carried out in halogenated hydrocarbons.

The temperatures can be varied within a certain range for the oxidation. In general, the oxidation is carried out between −20° C. and 130° C., preferably between 0° C. and 120° C.

In carrying out the oxidation, the starting compound of the formula (Ic) is in general reacted with the particular calculated amount or with a slight excess of oxidising agent. Working up is in each case effected by customary methods.

Formula (IV) provides a general definition of the phenol derivatives required as starting substances in carrying out process (b) according to the invention. In this formula, $R^3$, $R^4$ and p preferably have those meanings which have already been mentioned as particularly preferred for these radicals and for this index in connection with the description of the compounds of the formula (Ib). $X^2$ preferably represents hydrogen, sodium or potassium.

The phenol derivatives of the formula (IV) are known, or they can be prepared in a simple manner by known processes.

Formula (V) provides a general definition of the halogenomethyl phenyl sulphides also required as starting substances in process (b) according to the invention. In this formula, $R^2$, $R^5$ and m preferably have those meanings which have already been mentioned as particularly preferred for these radicals and for this index in connection with the description of the compounds of the formula (Ib). Hal preferably represents chlorine or bromine.

The halogenomethyl phenyl sulphides of the formula (V) are known, or they can be prepared in a simple manner by known processes (compare Liebigs Ann. 563, 54 (1949)).

Acid acceptors which can be used in carrying out process (b) according to the invention are all the acid-binding agents customarily suitable for such reactions. Preferred acid-binding agents which can be used are all those acid acceptors which have already been mentioned as acid binders which can preferably be used in connection with the description of process (a) according to the invention.

Possible diluents in carrying out process (b) according to the invention are virtually all the inert organic solvents. Solvents which can preferably be used are alcohols, such as methanol and ethanol, and furthermore ethers, such as dioxane and tetrahydrofuran, as well as ketones, such as acetone, and also amides, such as dimethylformamide, and finally aliphatic or aromatic, optionally halogenated hydrocarbons, such as pentane, hexane, heptane, cyclohexane, petroleum ether, benzine, ligroin, benzene, toluene, xylene, methylene chloride, ethylene chloride, chloroform, carbon tetrachloride, chlorobenzene and o-dichlorobenzene.

The reaction temperatures can be varied within a substantial range in process (b) according to the invention. In general, the reaction is carried out at temperatures between 0° C. and 80° C., preferably between 20° C. and 60° C.

Process (b) according to the invention is in general carried out under normal pressure. However, it is also possible to carry out the process under increased or reduced pressure.

For carrying out process (b) according to the invention, the starting substances of the formulae (IV) and (V) are generally employed in approximately equimolar amounts. However, it is also possible to use one of the two components, preferably the phenol derivative of the formula (IV), in excess. Working up is effected by customary methods. If an excess of phenol derivative of the formula (IV) has been used in the reaction, it is recommended to separate off excess phenol derivative by shaking the reaction mixture with aqueous alkali metal hydroxide solution.

If it is intended to prepare those compounds of the formula (Ib) in which n represents 1 or 2 in process (b) according to the invention, the oxidation of the compounds of the formula (Ic) is carried out as has already been mentioned in connection with the description of process (a) according to the invention.

Formula (VI) provides a general definition of the sulphinic acid salts required as starting substances in process (c) according to the invention. In this formula, $R^2$, $R^5$ and m preferably have those meanings which have already been mentioned as particularly preferred for these radicals and for this index in connection with the description of the compounds of the formula (Ib). M preferably represents sodium or potassium.

The sulphinic acid salts of the formula (VI) are known, or they can be prepared in a simple manner by known methods (compare Houben-Weyl "Methoden der Organischen Chemie" ("Methods of Organic Chemistry"), Volume IX, g. Thieme-Verlag, Stuttgart, 1955).

The halogenomethyl phenyl ethers of the formula (III) also required as starting substances in process (c) according to the invention have already been mentioned in connection with the description of process (b) according to the invention.

Catalysts which can be used in process (c) according to the invention are all the reaction accelerators customary for such reactions. Preferred reaction accelerators which can be used are inorganic iodine compounds, such as sodium iodide or potassium iodide.

Diluents which can be used in carrying out process (c) according to the invention are all the inert organic solvents. Preferred solvents which can be used are alcohols, such as ethanol and propanol, ethers, such as dioxane and tetrahydrofuran, and furthermore hydrocarbons, such as toluene, and also halogenohydrocarbons, such as chloroform, as well as ketones, such as acetone.

The reaction temperatures can be varied within a substantial range in process (c) according to the invention.

In general, the reaction is carried out at temperatures between 20° C. and 100° C., preferably between 40° C. and 80° C.

Process (c) according to the invention is in general carried out under normal pressure. However, it is also possible to carry out the process under increased or reduced pressure.

For carrying out process (c) according to the invention, the starting substances of the formulae (VI) and (III) are in general employed in approximately equimolar amounts. However, it is also possible to use one of the two components, preferably the sulphinic acid salt of the formula (VI), in excess. If a catalyst is used, about 0.001 to 0.1 mol of catalyst is employed per mol of halogenomethyl phenyl ether of the formula (III). Working up and isolation of the reaction products in process (c) according to the invention are effected by customary methods.

The formula (Ie) provides a definition of the compounds required as starting substances in process (d) according to the invention. In this formula, n represents 0, 1 or 2. These compounds are known, or they can be prepared by the abovementioned processes according to the invention.

The formula (VIII) provides a general definition of the compounds required as reaction components in process (d, variant α) according to the invention. In this formula, $R^7$ preferably represents alkyl with 2 to 8 carbon atoms, alkenyl with 2 to 8 carbon atoms, alkoxyalkyl with 1 to 4 carbon atoms in the alkoxy group and 1 to 4 carbon atoms in the alkyl part, alkylthioalkyl with 1 to 4 carbon atoms in the alkylthio group and 1 to 4 carbon atoms in the alkyl part, or the radical of the formula —$CH_2$—O—($CH_2$—$CH_2$—O)$_q$—Alk, in which Alk represents alkyl with 1 to 4 carbon atoms and q represents 0, 1 or 2.

The compounds of the formula (VII) are known.

Preferred bases which can be used in carrying out process (d, variant α) according to the invention are alkali metal hydroxides, such as sodium hydroxide or potassium hydroxide, and alkali metal alcoholates, in particular sodium or potassium alcoholates. In many cases, the potassium or sodium alcoholate of that alcohol of the formula (VII) which also functions as the reaction component is advantageously used.

Possible diluents in carrying out process (d, variant α) according to the invention are inert organic solvents, such as methylene chloride, toluene, xylene or ether, or an excess of the compound of the formula (VII) which functions as the reaction component.

The reaction temperatures can be varied within a substantial range in process (d, variant α) according to the invention. In general, the reaction is carried out at temperatures between 50° C. and 200° C., preferably between 80° and 160° C.

Process (d, variant α) according to the invention is carried out either under normal pressure or under increased pressure. It is advantageously carried out in a pressure vessel under the particular autogenous pressure of the reaction mixture.

In carrying out process (d, variant α) according to the invention, in general a large excess of a compound of the formula (VII) is employed per mol of a compound of the formula (Ie), so that the former can simultaneously serve as the diluent. In addition, a catalytic amount of a base is added.

In many cases, it is advisable to prepare the base at the start of the reaction by dissolving metallic sodium or potassium in the compound of the formula (VII), and then adding the component (Ie). In order to achieve as complete a conversion as possible, it is advantageous to strip off the diluent and the compound of the formula (VII) after some hours and to replace these again by a corresponding amount of the component of the formula (VII), if necessary mixed with an additional diluent. Working up is effected by customary methods. In general, a procedure is followed in which the reaction mixture is concentrated by stripping off the highly volatile constituents under reduced pressure, water and an organic solvent of low water-miscibility are added to the residue which remains and the organic phase is separated off, washed and, if appropriate after prior filtration and drying, concentrated.

The formula (VIII) provides a definition of the bases required as reaction components in process (d, variant β) according to the invention. In this formula, $M^1$ preferably represents a sodium or potassium cation or one equivalent of a magnesium or calcium cation.

Preferred possible diluents in carrying out the first stage (ester hydrolysis) of process (d, variant β) according to the invention are aromatic hydrocarbons, such as toluene or xylene, and also alcohols, such as methanol or ethanol, and furthermore ethers, such as dioxane, and moreover nitriles, such as acetonitrile, and also mixtures of organic solvents and water.

The temperatures can be varied within a substantial range in carrying out the ester hydrolysis in the first stage of process (d, variant β) according to the invention. In general, the reaction is carried out at temperatures between 0° C. and 160° C., preferably between 20° C. and 140° C.

All the customary strong acids can be used in the ester hydrolysis in the first stage of process (d, variant β) according to the invention. Mineral acids, such as hydrochloric acid or sulphuric acid, can preferably be used.

In carrying out the ester hydrolysis in the first stage of process (d, variant β) according to the invention, a procedure is in general followed in which the ester of the formula (Ie) is treated with an equivalent amount or with an excess of base in the presence of a diluent at the particular desired temperature. Working up is effected by customary methods. In general, a procedure is followed in which the reaction mixture is concentrated by stripping off the solvent under reduced pressure, the residue which remains is taken up in water, the mixture is acidified with mineral acid, such as, for example, hydrochloric acid or sulphuric acid, and the acid which thereby separates out is separated off.

If preparation of salts is intended, the acids initially obtained are treated with the paticular required base of the formula (VIII) in the presence of a diluent in the second stage of process (d, variant β). Preferred possible diluents here are water or watermiscible organic solvents.

The temperatures can likewise be varied within a substantial range in carrying out the second stage of process (d, variant β) according to the invention. In general, the reaction is carried out at temperatures between 0° C. and 60° C., preferably between 10° C. and 50° C.

In carrying out the second stage of process (d, variant β) according to the invention, a procedure is in general followed in which the acid of the formula (I) is reacted with an equivalent amount of base in an aqueous medium. For working up, the reaction mixture is in general evaporated and the residue which remains is dried.

The active compounds which can be used according to the invention engage in the metabolism of the plants and can therefore be employed as growth regulators.

Experience to date of the mode of action of plant growth regulators has shown that an active compound can also exert several different actions on plants. The actions of the compounds depend essentially on the point in time at which they are used, relative to the stage of development of the plant, and on the amounts of active compound applied to the plants or their environment and the way in which the compounds are applied. In every case, growth regulators are intended to influence the crop plants in the particular manner desired.

Plant growth-regulating compounds can be employed, for example, to inhibit vegetative growth of the plants. Such inhibition of growth is inter alia of economic interest in the case of grasses, since it is thereby possible to reduce the frequency of cutting the grass in ornamental gardens, parks and sportsground, at verges, at airports or in fruit orchards. The inhibition of growth of herbaceous and woody plants at verges and in the vicinity of pipelines or overland lines or, quite generally, in areas in which heavy additional growth of plants is undesired, is also of importance.

The use of growth regulators to inhibit the growth in length of cereals is also important. The danger of lodging of the plants before harvesting is thereby reduced or completely eliminated. Furthermore, growth regulators can strengthen the stem of cereals, which again counteracts lodging. Use of growth regulators for shortening and strengthening the stem enables higher amounts of fertiliser to be applied to increase the yield, without danger of the cereal lodging.

In the case of many crop plants, inhibition of the vegetative growth makes denser planting possible, so that greater yields per area of ground can be achieved. An advantage of the smaller plants thus produced is also that the crop can be worked and harvested more easily.

Inhibition of the vegetative growth of plants can also lead to increase in yield, since the nutrients and assimilates benefit blossoming and fruit formation to a greater extent than they benefit the vegetative parts of plants.

Promotion of vegetative growth can also frequently be achieved with growth regulators. This is of great utility if it is the vegetative parts of the plants which are harvested. Promoting the vegetative growth can, however, also simultaneously lead to a promotion of generative growth, since more assimilates are formed, so that more fruit, or larger fruit, is obtained.

Increases in yield can in some cases be achieved by affecting the plant metabolism, without noticeable changes in vegetative growth. A change in the composition of plants, which in turn can lead to a better quality of the harvested products, can furthermore be achieved with growth regulators. Thus it is possible, for example, to increase the content of sugar in sugar beet, sugar cane, pineapples and citrus fruit or to increase the protein content in soya and cereals. Using growth regulators it is also possible, for example, to inhibit the degradation of desired constituents, such as, for example, sugar in sugar beet or sugar cane, before or after harvesting. It is also possible favourably to influence the production of the efflux of secondary plant constituents. The stimulation of latex flux in rubber trees may be mentioned as an example.

Parthenocarpous fruit can be formed under the influence of growth regulators. Furthermore, the gender of the flowers can be influenced. Sterility of the pollen can also be produced, which is of great importance in the breeding and preparation of hybrid seed.

Branching of plants can be controlled by using growth regulators. On the one hand, by breaking the apical dominance the development of side shoots can be promoted, which can be very desirable, especially in the cultivation of ornamental plants, also in connection with growth inhibition. On the other hand, however, it is also possible to inhibit the growth of side shoots. There is great interest in this action, for example, in the cultivation of tobacco or in the planting of tomatoes.

The amount of leaf on plants can be controlled, under the influence of growth regulators, so that defoliation of the plants at a desired point in time is achieved. Such defoliation is of great importance in the mechanical harvesting of cotton, but is also of interest for facilitating harvesting in other crops, such as, for example, in viticulture. Defoliation of the plants can also be carried out to lower the transpiration of plants before they are transplanted.

The shedding of fruit can also be controlled with growth regulators. On the one hand, it is possible to prevent premature shedding of fruit. However, on the other hand, shedding of fruit, or even the fall of blossom, can be promoted up to a certain degree (thinning out) in order to interrupt the alternance. By alternance there is understood the peculiarity of some varieties of fruit to produce very different yields from year to year, for endogenic reasons. Finally, using growth regulators it is possible to reduce the force required to detach the fruit at harvest time so as to permit mechanical harvesting or facilitate manual harvesting.

Using growth regulators, it is furthermore possible to achieve can accleration or retardation of ripening of the harvest product, before or after harvesting. This is of particular advantage, since it is thereby possible to achieve optimum adaptation to market requirements. Furthermore, growth regulators can at times improve the coloration of fruit. In addition, concentrating the ripening within a certain period of time is also achievable with the aid of growth regulators. This provides the preconditions for being able to carry out complete mechanical or manual harvesting in only a single pass, for example in the case of tobacco, tomatoes or coffee.

Using growth regulators, it is furthermore possible to influence the latent period of seeds or buds of plants, so that the plants, such as, for example, pineapple or ornamental plants in nurseries, germinate, shoot or bloosm at a time at which they normally show no readiness to do so. Retarding the shooting of buds or the germination of seeds with the aid of growth regulators can be desirable in regions where frost is a hazard, in order to avoid damage by late frosts.

Finally, the resistance of plants to frost, drought or a high salt content in the soil can be induced with growth regulators. Cultivation of plants in regions which are usually unsuitable for this purpose thereby becomes possible.

The active compounds which can be used according to the invention not only are suitable for regulating plant growth but moreover can also be used as synergists for insecticides and for combating fungi.

The active compounds can be converted to the customary formulations, such as solutions, emulsions, suspensions, powders, foams, pastes, granules, aerosols, very fine capsules in polymeric substances and in coating compositions for seed, as well as ULV formulations.

These formulations are produced in known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water. By liquefied gaseous extenders or carriers are meant liquids which are gaseous at normal temperature and under normal pressure, for example aerosol propellants, such as halogenated hydrocarbons as well as butane, propane, nitrogen and carbon dioxide. As solid carriers there are suitable: for example, ground natural minerals, such as kaolins, clays, talc, chalk, quartz, attapulgite, montmorillonite or diatomaceous earth, and ground synthetic minerals, such as highly-dispered silicic acid, alumina and silicates. As solid carriers for granules there are suitable: for example, crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks. As emulsifying and/or foam-forming agents there are suitable: for example, non-ionic an anionic emulsifiers, such as polyoxyethylene-fatty acid esters, polyoxyethylene-fatty alcohol ethers, for example alkylaryl polyglycol ethers, alkylsulphonates, alkyl-sulphates, aryl-sulphonates as well as albumin hydrolysation products. As dispersing agents there are suitable: for example, ligninsulphite waste liquors ad methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs and metal phthalocyaninde dyestuffs, and trace nutrients such as salts of iron, manganese, boron, copper, cobalt, molybdenum and zinc.

The formulations in general contain between 0.1 and 95% by weight of active compound, preferably between 0.5 and 90%.

The active compounds which can be used according to the invention can be present in the formulations as a mixture with other known active compounds, such as fungicides, insecticides, acaricides and herbicides, and also as mixtures with fertilisers and other growth regulators.

The active compounds can be used as such, in the form of their formulations or as the use forms prepared therefrom, such as ready-to-use solutions, emulsifiable concentrates, emulsions, foams, suspensions, wettable powders, pastes, soluble powders, dusting agents and granules. They are used in the customary manner, for example by watering, spraying, atomising, scattering, dusting, foaing, coating and the like. Furthermore, it is possible to apply the active compounds in accordance with the ultra-low volume process or to inject the active compound preparation or the active compound itself into the soil. It is also possible to treat the seeds of plants.

The amounts applied can be varied within a substantial range. In general, 0.01 to 50 kg, preferably 0.05 to 10 kg, of the active compound are employed per hectare of soil surface.

As regards the time of application, the rule is that the growth regulators are applied within a preferred period of time, the exact definition of which depends on the climatic and vegetative circumstances.

The preparation and use of the phenoxy-methane derivatives which can be used according to the invention can be seen from the following examples.

Preparation Examples

EXAMPLE 1

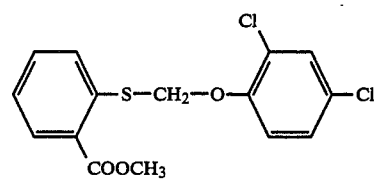

A solution of 28 g (0.25 mol) of potassium tert.-butylate in 120 ml of tetrahydrofuran was slowly added dropwise to a solution of 33.6 g (0.2 mol) of methyl 2-mercapto-benzoate in 50 ml of tetrahydrofuran at 5° C. At the end of the dropwise addition, stirring was continued at 5° C. for a further 30 minutes. The solid product precipitated was filtered off with suction and dissolved in 100 ml of dimethylformamide. A solution of 42.3 g (0.2 mol) of chloromethyl 2,4-dichlorophenyl ether in 60 ml of dimethylformamide was added dropwise to this solution, while stirring at 25° C. The mixture was subsequently stirred at 30° C. for 1 hour and then worked up by stirring into 1.5 liters of ice-water. The suspension thereby formed was filtered off with suction and the solid product precipitated was dried in air. 62 g (90.4% of theory) of 1-(2,4-dichlorophenoxy)-1-(2-methoxycarbonyl-phenylthio)-methane were obtained in this manner in the form of colourless crystals of melting point 122°–124° C.

EXAMPLE 2

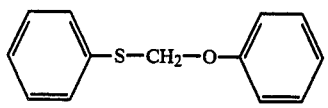

A solution of 47.5 g (0.3 mol) of chloromethyl phenyl sulphide in 50 ml of dimethylformamide was added dropwise to a solution of 40 g (0.34 mol) of sodium phenolate in 200 ml of dimethylformamide at room temperature in the course of 30 minutes, while stirring. The temperature of the reaction mixture thereby rose from 24° C. to 35° C. The mixture was subsequently stirred at room temperature for 14 hours and then concentrated by stripping off the solvent under reduced pressure. The oil which remained was washed successively with water, 0.1N aqueous sodium hydroxide solution and water and, after drying sodium sulphate, subjected to fractional vacuum distillation. 50 g (77.2% of theory) of phenoxy-phenylthiomethane were obtained in this manner in the form of a colourless liquid of boiling point 112°–117° C./0.16 mm Hg.

EXAMPLE 3

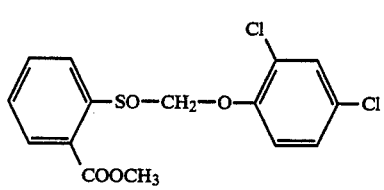

7 g (0.072 mol) of 35% strength aqueous hydrogen peroxide solution were added dropwise to a solution of 17.1 g (0.05 mol) of 1-(2,4-dichlorophenoxy)-1-2-methoxycarbonyl-phenylthio)-methane in 100 ml of glacial acetic acid at 70° C. in the course of 30 minutes, while stirring. The reaction mixture was subsequently stirred at 70° C. for 1 hour and then cooled to room temperature and stirred into 500 ml of ice-water. The crystals precipitated were filtered off with suction, washed with water and dried over potassium hydroxide in a desiccator. 17 g (95% of theory) of 1-(2,4-dichloro-phenoxy)-1-(2-methoxycarbonyl-phenylsulphinyl)-methane were obtained in this manner in the form of colourless crystals of melting point 64°–67° C.

EXAMPLE 4

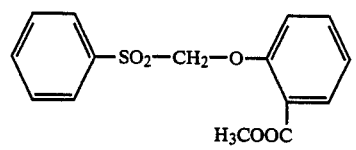

50 g (0.515·mol) of 35% strength aqueous hydrogen peroxide solution were added dropwise to a solution of 48 g (0.175 mol) of 1-(2-methoxycarbonyl-phenoxy)-1-phenylthio-methane in 180 methane of glacial acetic acid at 40°–50° C. in the course of 30 minutes, while stirring.

The reaction mixture was subsequently stirred at 50° C. for 14 hours and then cooled and stirred into 1 liter of ice-water. The crystals precipitated were filtered off with suction and dried over potassium hydroxide in a desiccator. 48.5 g (90.5% of theory) of 1-(2-methoxy-carbonyl-phenoxy)-1-(phenylsulphonyl)-methane were obtained in this manner in the form of colourless crystals of melting point 61°–62° C.

EXAMPLE 5

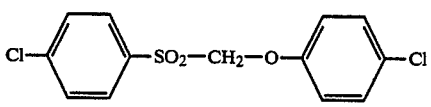

2.84 g (0.02 mol) of chloromethyl[4-chloro-phenyl]ether were added dropwise to a suspension of 4 g (0.021 mol) of sodium (4-chlorobenzene)-sulphinate in 50 ml of acetone at room temperature, while stirring. After a catalytic amount of sodium iodide had then been added, the mixture was subsequently stirred, first at room temperature for 2 hours and then at 50° C. for 4 hours. For working up, the reaction mixture was then concentrated by stripping off the solvent under reduced pressure and the oily residue which remained was taken up in methylene chloride. After the organic phase had been washed with water, the solvent was stripped off under reduced pressure and a little ethanol was added to the residue which remained. A solid product precipitated in the cold, and was filtered off with suction and dried. 0.84 g (15% of theory) of 1-(4-chloro-phenoxy)-1-(4-chloro-phenyl-sulphonyl)-methane was obtained in this manner in the form of colourless crystals of melting point 114° C.

The phenoxy-methane derivatives listed by way of their formulae in the table which follows were also prepared by the methods described in Examples 1 to 5.

TABLE 1

| Example No. | $R^1$ | $R^2_m$ | $R^3_p$ | $R^4$ | n | Melting point (°C.) or boiling point or refractive index |
|---|---|---|---|---|---|---|
| 5 | 4-Cl | H | H | H | 0 | boiling point 129/0.2 |
| 6 | 4-CH$_3$ | H | H | H | 0 | boiling point 110–112/0.16 |

TABLE 1-continued (I)

$$\text{structure shown: } R^1\text{-substituted phenyl-}S(O)_n\text{-}CH_2\text{-}O\text{-phenyl with }(R^3)_p, R^4; (R^2)_m$$

| Example No. | $R^1$ | $R^2{}_m$ | $R^3{}_p$ | $R^4$ | n | Melting point (°C.) or boiling point or refractive index |
|---|---|---|---|---|---|---|
| 7 | 4-Cl | H | 2-phenyl | H | 0 | melting point 38–40° C. |
| 8 | 4-Cl | H | H | H | 2 | melting point 78–79° C. |
| 9 | 4-CH$_3$ | H | H | H | 2 | melting point 73–75° C. |
| 10 | H | H | H | H | 2 | melting point 58–60° C. |
| 11 | 4-Cl | H | 2-phenyl | H | 2 | melting point 113–114° C. |
| 12 | 4-Cl | H | 4-Cl | 3-CH$_3$ | 0 | $n_D^{20}$ 1.6160 |
| 13 | 4-CH$_3$ | H | 4-Cl | 3-CH$_3$ | 0 | $n_D^{20}$ 1.6300 |
| 14 | H | H | 4-Cl | 3-CH$_3$ | 0 | $n_D^{20}$ 1.6300 |
| 15 | 4-Cl | H | 4-Cl | H | 0 | $n_D^{20}$ 1.6211 |
| 16 | 4-CH$_3$ | H | 4-Cl | H | 0 | melting point 41–43° C. |
| 17 | H | H | 4-Cl | H | 0 | $n_D^{20}$ 1.6125 |
| 18 | 4-Cl | H | 4-Cl | 3-CH$_3$ | 2 | melting point 100–101° C. |
| 19 | 4-CH$_3$ | H | 4-Cl | 3-CH$_3$ | 2 | melting point 99–100° C. |
| 20 | H | H | 4-Cl | 3-CH$_3$ | 2 | melting point 99–100° C. |
| 21 | 4-CH$_3$ | H | 4-Cl | H | 2 | melting point 88° C. |
| 22 | H | H | 4-Cl | H | 2 | melting point 99° C. |
| 23 | H | H | 2-phenyl | H | 0 | $n_D^{20}$ 1.6435 |
| 24 | 4-CH$_3$ | H | 2-phenyl | H | 0 | $n_D^{20}$ 1.6342 |
| 25 | H | H | 2-phenyl | H | 2 | melting point 102–103° C. |
| 26 | 4-CH$_3$ | H | 2-phenyl | H | 2 | melting point 120–121° C. |
| 27 | 4-C$_4$H$_9$—tert. | H | H | H | 0 | $n_D^{20}$ 1.5905 |
| 28 | " | H | 4-Cl | 3-CH$_3$ | 0 | $n_D^{20}$ 1.6030 |
| 29 | " | H | H | H | 2 | melting point 63–65° C. |
| 30 | " | H | 4-Cl | 3-CH$_3$ | 2 | melting point 80–84° C. |
| 31 | 4-Cl | H | 2-OC$_3$H$_7$—iso | H | 0 | $n_D^{20}$ 1.5880 |
| 32 | 2-COOCH$_3$ | H | 4-Cl | H | 0 | melting point 59° C. |
| 33 | 4-CH$_3$ | H | 3-CH$_3$ | H | 0 | boiling point 127–128/0.5 |
| 34 | 4-CH$_3$ | H | 2-Cl | 4-Cl | 0 | melting point 40–41° C. |
| 35 | 4-CH$_3$ | H | 2-OC$_3$H$_7$—iso | H | 0 | $n_D^{20}$ 1.5805 |
| 36 | 4-Cl | H | H | 2-COOCH$_3$ | 2 | melting point 90–91° C. |
| 37 | 4-Cl | H | 2-OC$_3$H$_7$—iso | H | 2 | melting point 72° C. |
| 38 | 4-CH$_3$ | H | 3-CH$_3$ | H | 2 | melting point 52° C. |
| 39 | 4-CH$_3$ | H | 2-Cl | 4-Cl | 2 | melting point 91° C. |
| 40 | 4-CH$_3$ | H | H | 2-COOCH$_3$ | 0 | melting point 63–65° C. |
| 41 | H | H | H | 2-COOCH$_3$ | 0 | melting point 41–43° C. |
| 42 | 4-Cl | H | 3-OCH$_3$ | H | 0 | $n_D^{20}$ 1.6230 |
| 43 | 4-CH$_3$ | H | H | 2-COOCH$_3$ | 2 | melting point 126–128° C. |
| 44 | 2-COOCH$_3$ | H | 2-Cl | 4-Cl | 2 | melting point 109–110° C. |
| 45 | 3-Cl | 4-Cl | H | 2-COOCH$_3$ | 0 | $n_D^{20}$ 1.6109 |
| 46 | 2-Cl | 5-Cl | H | 2-COOCH$_3$ | 0 | melting point 46–48° C. |

TABLE 1-continued $$\text{(I)}$$

Structure: Ar(R¹)(R²)ₘ—S(O)ₙ—CH₂—O—Ar(R³)ₚ(R⁴)

| Example No. | R¹ | R²ₘ | R³ₚ | R⁴ | n | Melting point (°C.) or boiling point or refractive index |
|---|---|---|---|---|---|---|
| 47 | 4-C₄H₉—tert. | H | H | 2-COOCH₃ | 0 | $n_D^{20}$ 1.5722 |
| 48 | H | H | H | 2-COOC₂H₅ | 0 | $n_D^{20}$ 1.5881 |
| 49 | H | H | H | 2-COO—C₄H₉—iso | 0 | $n_D^{20}$ 1.5720 |
| 50 | H | H | H | 2-COO—C₃H₇—iso | 0 | $n_D^{20}$ 1.5721 |
| 51 | H | H | H | 2-COO—C₅H₁₁—iso | 0 | $n_D^{20}$ 1.5650 |
| 52 | H | H | H | 2-COO—C₆H₅ (phenyl) | 0 | $n_D^{20}$ 1.6052 |
| 53 | H | H | H | 2-CO—NH₂ | 0 | melting point 127–128° C. |
| 54 | H | H | H | 4-COOCH₃ | 0 | melting point 67–68° C. |
| 55 | H | H | H | 4-COO—C₂H₅ | 0 | $n_D^{20}$ 1.5716 |
| 56 | H | H | H | 4-COO—C₃H₇—n | 0 | $n_D^{20}$ 1.5690 |
| 57 | H | H | 4-NO₂ | 2-CN | 0 | melting point 72–74° C. |
| 58 | H | H | 2,6-Br₂ | 4-CN | 0 | melting point 85–87° C. |
| 59 | H | H | H | 4-CN | 0 | $n_D^{20}$ 1.5521 |
| 60 | H | H | H | 2-COOCH₃ | 1 | $n_D^{20}$ 1.5800 |
| 61 | H | H | H | 2-COOC₂H₅ | 1 | $n_D^{20}$ 1.5760 |
| 62 | H | H | H | 2-COOC₂H₅ | 2 | $n_D^{20}$ 1.5597 |
| 63 | H | H | H | 2-COOC₃H₇—iso | 1 | $n_D^{20}$ 1.5724 |
| 64 | H | H | H | 2-COOC₃H₇—iso | 2 | melting point 55–57° C. |
| 65 | H | H | H | 2-COOC₅H₁₁—iso | 1 | $n_D^{20}$ 1.5600 |
| 66 | H | H | H | 2-COOC₅H₁₁—iso | 2 | $n_D^{20}$ 1.5413 |
| 67 | H | H | 6-CH₃ | 2-COOCH₃ | 0 | $n_D^{20}$ 1.5890 |
| 68 | H | H | 6-CH₃ | 2-COOCH₃ | 1 | $n_D^{20}$ 1.5822 |

EXAMPLE 69

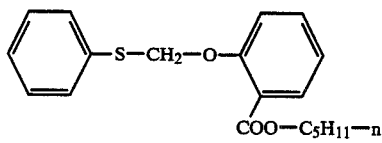

0.5 g (0.022 mol) of sodium was dissolved in 250 ml of anhydrous n-amyl alcohol. This solution was then introduced into a VA steel autoclave of 0.7 liter capacity together with 25 g (0.091 mol) of methyl 2-(phenylthio-methoxy)-benzoate and the mixture was heated at 140° C. for 18 hours. The reaction mixture was then taken out of the autoclave and concentrated under reduced pressure. A furter 250 ml of anhydrous n-amyl alcohol were added and the mixture was again heated at 140° C. in an autoclave for 18 hours. After this procedure had been repeated again, the reaction mixture was worked up by evaporating under reduced pressure and taking up the residue in water and methylene chloride. The organic phase was separated off, washed neutral with water, filtered over a thin layer of silica gel 60, particle size 0.063–0.1 mm, and concentrated by stripping off the solvent under reduced pressure. 24.3 g (80.8% of theory) of n-amyl 2-(phenylthio-methoxy)-benzoate were obtained in this manner in the form of a liquid of refractive index $n_D^{20}$ 1.5575.

EXAMPLE 70

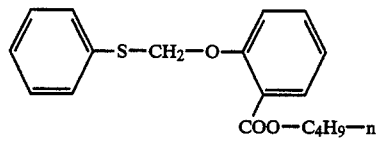

0.5 g (0.022 mol) of sodium was dissolved in 250 ml of anhydrous n-butanol. This solution was then introduced into a VA steel autoclave of 0.7 liter capacity together with 25 g (0.091 mol) of methyl 2-phenylthio-methoxy)-benzoate, and the mixture was heated at 120° C. for 2 hours. The reaction mixture was then worked up by evaporating under reduced pressure and taking up the residue in water and methylene chloride. The organic phase was separated off, washed neutral with water, filtered over a thin layer of silica gel 60, particle size 0.063–0.2 mm and concentrated by stripping off the solvent under reduced pressure. 22 g (76.5% of theory) of n-butyl 2-(phenylthio-methoxy)-benzoate were obtained in this manner in the form of a liquid of refractive index $n_D^{20}$ 1.5775.

The phenoxy-methane derivatives listed by way of their formulae in the following table were also prepared by the method described in Examples 69 and 70:

TABLE 2

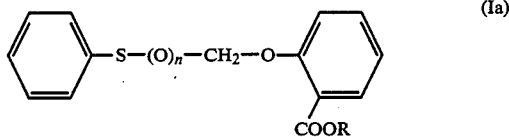
(Ia)

| Example No. | R | n | Refractive index or melting point |
|---|---|---|---|
| 71 | —$C_3H_7$—n | 0 | $n_D^{20}$ = 1.5828 |
| 72 | —$C_8H_{17}$—n | 0 | $n_D^{20}$ = 1.5348 |
| 73 | —$C_6H_{13}$—n | 0 | $n_D^{20}$ = 1.5430 |
| 74 | —$CH_2$—$CH_2$—O—$CH_3$ | 0 | mp. = 40–42° C. |
| 75 | —$CH_2$—$CH_2$—O—$C_4H_9$—n | 0 | $n_D^{20}$ = 1.5620 |
| 76 | —$CH_2$—$CH_2$—O—$C_2H_5$ | 0 | $n_D^{20}$ = 1.5682 |
| 77 | —$CH_2$—CH=$CH_2$ | 0 | $n_D^{20}$ = 1.5952 |
| 78 | —$CH_2$—$CH_2$—S—$C_5H_5$ | 0 | $n_D^{20}$ = 1.5390 |
| 79 | —$(CH_2)_2$—O—$(CH_2)_2$—$OCH_3$ | 0 | $n_D^{20}$ = 1.5621 |
| 80 | —$(CH_2)_2$—O—$C_3H_7$—iso | 0 | $n_D^{20}$ = 1.5520 |

EXAMPLE 81

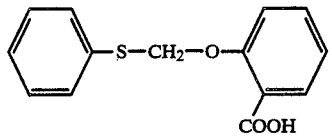

137 g (0.5 mol) of methyl 2-(phenylthio-methoxy)-benzoate were added to a solution of 33.6 g (0.6 mol) of potassium hydroxide in 500 ml of methanol, and the mixture was heated at the boiling point for 3 hours, with stirring. The mixture was then worked up by stripping off the solvent under reduced pressure, taking up the residue in 1 liter of water and briefly extracting the resulting solution with ether. The aqueous phase was then covered with a layer of 300 ml of ether and was acidified to a pH value of 2 by addition of 2 normal aqueous hydrochloric acid, with shaking. The phases were separated and the aqueous phase was extracted with two more 300 ml portions of ether. After the combined organic phases had been dried over sodium sulphate, they were concentrated by stripping off the solvent under reduced pressure. 126 g (96.9% of theory) of 2-(phenylthio-methoxy)-benzoic acid were contained in this manner in the form of a colourless oil which, when triturated, crystallised completely. Melting point=57°–59° C.

EXAMPLE 82

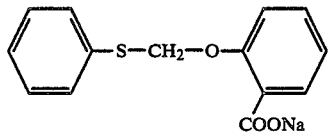

126 g (0.48 mol) of 2-(phenylthio-methoxy)-benzoic acid were dissolved in 500 ml of water, with addition of 19.18 g (0.48 mol) of sodium hydroxide. The reaction mixture was stirred at room temperature for 30 minutes and then evaporated completely at 60° C. under reduced pressure. The colourless pulverulent product which remained was dried at 100° C. under reduced pressure for 16 hours. 133.5 g (98.6% of theory) of sodium 2-(phenylthio-methoxy)-benzoate of melting point 204°–207° C. were obtained in this manner.

EXAMPLE 83

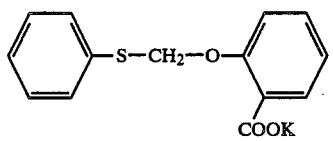

Potassium 2-(phenylthio-methoxy)-benzoate was also prepared by the method described in Example 82. Melting point: 240° C. (decomposition).

The phenoxy-methane derivatives listed by way of their formulae in Table 3 were also prepared by the methods described in Examples 3 and 4.

TABLE 3

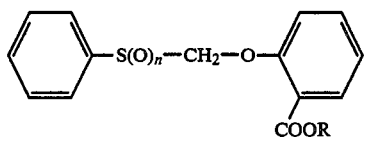
(Ia)

| Example No. | R | n | Refractive index [$n_D^{20}$] or melting point [°C.] |
|---|---|---|---|
| 84 | —$CH_2$—CH=$CH_2$ | 1 | 1.5926 |
| 85 | —$CH_2$—CH=$CH_2$ | 2 | 1.5703 |
| 86 | —$(CH_2)_7$—$CH_3$ | 2 | 1.5220 |
| 87 | —$(CH_2)_7$—$CH_3$ | 1 | 1.5430 |
| 88 | —$(CH_2)_5$—$CH_3$ | 1 | 1.5290 |
| 89 | —$(CH_2)_5$—$CH_3$ | 2 | 52–54 |
| 90 | —$CH_2CH_2$—$OCH_3$ | 2 | 1.5625 |
| 91 | —$CH_2CH_2$—$OCH_3$ | 1 | 1.5765 |
| 92 | —$CH_2CH_2OCH_2CH_2$—$OCH_3$ | 1 | 1.5668 |
| 93 | —$CH_2CH_2OCH_2CH_2$—$OCH_3$ | 2 | 1.5490 |
| 94 | —$CH_2CH_2$—$OCH(CH_3)_2$ | 1 | 1.5530 |
| 95 | —$CH_2CH_2$—$OCH(CH_3)_2$ | 2 | 1.5350 |
| 96 | H | 1 | 107–8 |
| 97 | H | 2 | 139–40 |
| 98 | K | 2 | 184–5 |
| 99 | Na | 2 | 105–7 |
| 100 | Na | 1 | 97–99 |
| 101 | K | 1 | 125–7 |

EXAMPLE A

Stimulation of the fixation of $CO_2$ in soya beans

Solvent: 30 parts by weight of dimethylformamide
Emulsifier: 1 part by weight of polyoxyethylene sorbitan monolaurate To produce a suitable preparation of active compound, 1 part by weight of active compound is mixed with the stated amounts of solvent and emulsifier and the mixture is made up to the desired concentration with water.

Soya bean plants are grown in a greenhouse until the first secondary leaf has unfolded completely. At this stage, the plants are sprayed with the preparations of active compound until dripping wet. In the further course of the experiment; the fixation of $CO_2$ in the plants is determined by customary methods. The values are compared with those of control plants, which have not been treated with the active compounds.

The figures of merit have the following meanings:
— denotes inhibition of the fixation of $CO_2$
0 denotes fixation of $CO_2$ as in the case of the control
+ denotes low stimulation of the fixation of $CO_2$ ++ denotes powerful stimulation of the fixation of $CO_2$ +++ denotes very powerful stimulation of the fixation of $CO_2$ The active compounds, active compound concentrations and test results can be seen from the following table.

TABLE A

| Stimulation of the fixation of $CO_2$ in soya beans | | |
|---|---|---|
| Active compound according to Example No. | Active compound concentration in % | Action |
| (13) | 0.05 | + |
| (15) | 0.05 | + |
| (18) | 0.05 | + |
| (41) | 0.05 | + |
| (44) | 0.05 | + |
| (46) | 0.05 | ++ |
| (74) | 0.05 | + |
| (77) | 0.05 | ++ |
| (80) | 0.05 | ++ |
| — (Control) | — | 0 |

EXAMPLE B

Inhibition of growth of barley

Solvent: 30 parts by weight of dimethylformamide
Emulsifier: 1 part by weight of polyoxyethylene sorbitan monolaurate To produce a suitable preparation of active compound, 1 part by weight of active compound is mixed with the stated amounts of solvent and emulsifier and the mixture is made up to the desired concentration with water.

Barley plants are grown in a greenhouse to the 2-leaf stage. In this stage, the plants are sprayed with the preparations of active compound until dripping wet. After 3 weeks, the additional growth of all the plants is measured and the inhibition of growth in percent of the additional growth of the control plants is calculated. 100% inhibition of growth means that growth has stopped and 0% denotes a growth corresponding to that of the control plants.

The active compounds, active compound concentrations and test results can be seen from the table which follows.

TABLE B

| Inhibition of growth of barley | | |
|---|---|---|
| Active compound according to Example No. | Active compound concentration in % | Inhibition of growth in % |
| (4) | 0.05 | 30 |
| (41) | 0.05 | 45 |
| (48) | 0.05 | 60 |
| (50) | 0.05 | 51 |
| (51) | 0.05 | 42 |
| (52) | 0.05 | 42 |
| (60) | 0.05 | 31 |
| (74) | 0.05 | 71 |
| (75) | 0.05 | 49 |
| (76) | 0.05 | 51 |
| (77) | 0.05 | 54 |
| (78) | 0.05 | 21 |
| (79) | 0.05 | 37 |
| (80) | 0.05 | 37 |
| (81) | 0.05 | 23 |
| (82) | 0.05 | 68 |
| (83) | 0.05 | 19 |
| — | — | 0 |

TABLE B-continued

| Inhibition of growth of barley | | |
|---|---|---|
| Active compound according to Example No. | Active compound concentration in % | Inhibition of growth in % |
| (Control) | | |

EXAMPLE C

Inhibition of growth of cotton

Solvent: 30 parts by weight of dimethylformamide
Emulsifier: 1 part by weight of polyoxyethylene sorbitan monolaurate To produce a suitable preparation of active compound, 1 part by weight of active compound is mixed with the stated amounts of solvent and emulsifier and the mixture is made up to the desired concentration with water.

Cotton plants are grown in a greenhouse until the 5th secondary leaf has unfolded completely. In this stage, the plants are sprayed with the preparations of active compound until dripping wet. After 3 weeks, the additional growth of the plants is measured and the inhibition of growth in percent of the additional growth of the control plants is calculated. 100% inhibition of growth means that growth has stopped and 0% denotes a growth corresponding to that of the control plants.

The active compounds, active compound concentrations and test results can be seen from the following table.

TABLE C

| Inhibition of growth of cotton | | |
|---|---|---|
| Active compound according to Example No. | Active compound concentration in % | Inhibition of growth in % |
| (30) | 0.05 | 33 |
| (59) | 0.05 | 72 |
| — (Control) | — | 0 |

EXAMPLE D

Formation of ethylene

Solvent: 30 parts by weight of dimethylformamide
Emulsifier: 1 part by weight of polyoxyethylene sorbitan monolaurate To produce a suitable preparation of active compound, 1 part by weight of active compound is mixed with the stated amounts of solvent and emulsifier and the mixture is made up to the desired concentration with water.

Pieces of leaf of identical size are punched from soya bean leaves. These are introduced into vessels which can be closed air-tight, together with 1 ml of the preparation of active compound or control solution. After 24 hours the ethylene which has collected in the vessels is determined by customary methods of detection. The evolution of ethylene from the pieces of leaf treated with the preparations of active compound is compared with the evolution of ethylene from the controls.

The figures of merit have the following meanings:

O denotes evolution of ethylene as in the case of the control

+ denotes slightly increased evolution of ethylene

++ denotes greatly increased evolution of ethylene

+++ denotes very greatly increased evolution of ethylene

The active compounds, active compound concentrations and test results can be seen from the following table.

TABLE D

| Active compound according to Example No. | Active compound concentration in % | Action |
|---|---|---|
| (41) | 0.001 | +++ |
| (50) | 0.001 | ++ |
| (52) | 0.001 | + |
| (56) | 0.001 | + |
| — (Control) | — | 0 |

EXAMPLE E

Influence on growth of sugar beet

Solvent: 30 parts by weight of dimethylformamide
Emulsifier: 1 part by weight of polyoxyethylene sorbitan monolaurate To produce a suitable preparation of active compound, 1 part by weight of active compound is mixed with the stated amounts of solvent and emulsifier and the mixture is made up to the desired concentration with water.

Sugar beet is grown in a greenhouse until formation of the cotyledons is complete. In this stage, the plants are sprayed with the preparations of active compound until dripping wet. After 14 days, the additional growth of the plants is measured and the influence on growth in percent of the additional growth of the control plants is calculated. 0% influence on growth denotes a growth which corresponds to that of the control plants. Negative values characterise an inhibition of growth in comparison to the control plants, whilst positive values characterise a promotion of growth in comparison to the control plants.

The active compounds, active compound concentrations and test results can be seen from the following table.

TABLE E

| Active compound according to Example No. | Active compound concentration in % | Influence on growth in % |
|---|---|---|
| (5) | 0.05 | +15 |
| (52) | 0.05 | +13 |
| (78) | 0.05 | +12 |
| | 0.003 | +12 |
| (79) | 0.05 | +4 |
| | 0.003 | +12 |
| (80) | 0.05 | +12 |
| — (Control) | — | 0 |

It will be understood that the specification and examples are illustrative but not limitative of the present invention and that other embodiments within the spirit and scope of the invention will suggest themselves to those skilled in the art.

What is claimed is:

1. Plant growth regulant composition comprising as an active ingredient a plant growth regulating effective amount of at least one phenoxymethane derivative of the formula

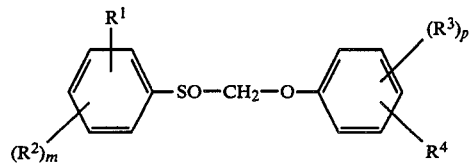

in which
R$^1$ represents hydrogen, alkyl, alkoxy, halogenoalkyl, halogenoalkoxy, alkoxycarbonyl, cycloalkoxycarbonyl or nitro,
R$^2$ represents hydrogen or alkyl,
R$^3$ represents hydrogen, alkyl, alkenyl, alkinyl, phenyl which is optionally substituted by alkyl and/or halogen, phenylalkyl which is optionally substituted by alkyl and/or halogen, alkoxy, phenoxy, halogenoalkyl, halogenoalkoxy, alkylthio, halogenoalkylthio, alkylsulphonyl, phenylthio, phenylsulphonyl or nitro,
R$^4$ represents hydrogen, alkyl, cycloalkoxycarbonyl, aminocarbonyl, alkylaminocarbonyl, dialkylaminocarbonyl, cycloalkylaminocarbonyl, dicycloalkyl-aminocarbonyl, phenoxycarbonyl which is optionally substituted by halogen and/or alkyl, cyano or the radical of the formula —COOR,
wherein
R represents hydrogen, an alkali metal cation, one equivalent of an alkaline earth metal cation, alkyl, alkenyl, alkoxyalkyl, alkylthioalkyl or the radical of the formula —CH$_2$—O—(CH$_2$—CH$_2$O)$_q$—Alk
wherein
Alk represent alkyl and
q represents 0, 1 or 2,
m represents 1, 2 or 3,
p represents 1, 2 or 3 and a plant growth regulant compatible diluent.

2. Plant growth regulant composition as claimed in claim 1 wherein in formula (I),
R$^1$ represents hydrogen, straight-chain or branched alkyl with 1 to 6 carbon atoms, straight-chain or branched halogenoalkyl with 1 to 6 carbon atoms and 1 to 5 halogen atoms, straight-chain or branched alkoxy with 1 to 6 carbon atoms, halogenoalkoxy with 1 to 6 carbon atoms and 1 to 5 halogen atoms, alkoxycarbonyl with 1 to 10 carbon atoms in the alkoxy group, cycloalkoxycarbonyl with 3 to 8 carbon atoms in the cycloalkyl group, nitro,
R$^2$ represents hydrogen, straight-chain or branched alkyl with 1 to 4 carbon atoms, fluorine, chlorine, bromine or iodine,
R$^3$ represents hydrogen, straight-chain or branched alkyl with 1 to 6 carbon atoms, straight-chain or branched alkenyl with 3 to 6 carbon atoms, straight-chain or branched alkinyl with 3 to 6 carbon atoms, phenyl which is optionally substituted by alkyl with 1 to 4 carbon atoms, fluorine, chlorine, bromine and/or iodine, benzyl which is optionally substituted by alkyl with 1 to 4 carbon atoms, fluorine, chlorine, bromine and/or iodine, alkoxy with 1 to 6 carbon atoms, phenoxy, halogenoalkyl with 1 to 6 carbon atoms and 1 to 5 halogen atoms, halogenoalkoxy with 1 to 6 carbons atoms and 1 to 5 halogen atoms, alkylthio with 1 to 6 carbon atoms, halogenoalkylthio with 1 to 6 carbon atoms and 1 to 5 halogen atoms, alkylsulphonyl with 1 to 6 carbon atoms, phenylthio, phenylsulphonyl or nitro, $R^4$ represents hydrogen, straight-chain or branched alkyl with 1 to 6 carbon atoms, cycloalkoxycarbonyl with up to 10 carbon atoms in the cycloalkyl group, aminocarbonyl, alkylaminocarbonyl with 1 to 6 carbon atoms in the alkyl group, dialkylaminocarbonyl with 1 to 6 carbon atoms in each alkyl group, cycloalkylaminocarbonyl with 3 to 8 carbon atoms in the cycloalkyl group, di-cycloalkylaminocarbonyl with 3 to 8 carbon atoms in each cycloalkyl group, phenoxycarbonyl which is optionally substituted by alkyl with 1 to 4 carbon atoms, fluorine, chlorine, bromine and/or iodine, cyano, or the radical of the formula —COOR, wherein R represents hydrogen, a sodium or potassium cation, one equivalent of a magnesium or calcium cation, alkyl with 1 to 10 carbon atoms, alkenyl with 2 to 10 carbon atoms, alkoxyalkyl with 1 to 6 carbon atoms in the alkoxy group and 1 to 6 carbon atoms in the alkyl part, alkylthioalkyl with 1 to 6 carbon atoms in the alkylthio group and 1 to 6 carbon atoms in the alkyl part, or the radical of the formula —CH$_2$—O—(CH$_2$—CH$_2$O)$_q$—Alk wherein Alk represents alkyl with 1 to 6 carbon atoms and q represents 0, 1 or 2, m represents 1 or 2, and p represents 1 or 2.

3. Plant growth regulant composition as claimed in claim 1 wherein in formula (I), $R^1$ represents hydrogen, straight-chain or branched alkyl with 1 to 4 carbon atoms, straight-chain or branched alkoxy with 1 to 4 carbon atoms, halogenoalkoxy with 1 to 3 carbon atoms and 1 to 5 fluorine, chlorine and/or bromine atoms, halogenoalkyl with 1 to 3 carbon atoms and 1 to 5 fluorine, chlorine and/or bromine atoms, alkoxycarbonyl with 1 to 4 carbon atoms in the alkoxy group, cycloalkoxycarbonyl with 3 to 6 carbon atoms in the cycloalkyl group, chlorine or nitro, $R^2$ represents hydrogen, straight-chain or branched alkyl with 1 to 4 carbon atoms, $R^3$ represents hydrogen, straight-chain or branched alkyl with 1 to 4 carbon atoms, straight-chain or branched alkenyl with 3 to 5 carbon atoms, straight-chain or branched alkinyl with 3 to 5 carbon atoms, phenyl which is optionally substituted by alkyl with 1 to 3 carbon atoms, fluorine, chlorine and/or bromine, benzyl which is optionally substituted by alkyl with 1 to 3 carbon atoms, fluorine, chlorine and/or bromine, alkoxy with 1 to 4 carbon atoms, phenoxy, halogenoalkyl with 1 to 3 carbon atoms and 1 to 5 fluorine, chlorine and/or bromine atoms, halogenoalkoxy with 1 to 3 carbon atoms and 1 to 5 fluorine, chlorine and/or bromine atoms, alkylthio with 1 to 4 carbon atoms, halogenoalkylthio with 1 to 3 carbon atoms and 1 to 5 fluorine, chlorine and/or bromine atoms, alkylsulphonyl with 1 to 4 carbon atoms, phenylthio, phenylsulphonyl or nitro, $R^4$ represents hydrogen, straight-chain or branched alkyl with 1 to 4 carbon atoms, cycloalkoxycarbonyl with 3 to 8 carbon atoms in the cycloalkyl group, aminocarbonyl, alkylaminocarbonyl with 1 to 4 carbon atoms in the alkyl group, dialkylaminocarbonyl with 1 to 4 carbon atoms in each alkyl group, cycloalkylaminocarbonyl with 3 to 7 carbon atoms, in the cycloalkyl group, dicycloalkyl-aminocarbonyl with 3 to 7 carbon atoms in each cycloalkyl group, phenoxycarbonyl which is optionally substituted by alkyl with 1 to 3 carbon atoms, fluorine, chlorine and/or bromine, cyano or the radical of the formula —COOR, wherein R represents hydrogen, a sodium or potassium cation, one equivalent of a magnesium or calcium cation, alkyl with 1 to 8 carbon atoms, alkenyl with 2 to 8 carbon atoms, alkoxyalkyl with 1 to 4 carbon atoms in the alkoxy group and 1 to 4 carbon atoms in the alkyl part, alkylthioalkyl with 1 to 4 carbon atoms in the alkylthio group and 1 to 4 carbon atoms in the alkyl part or the radical of the formula —CH$_2$—O—(CH$_2$—CH$_2$—O)$_q$—Alk, wherein Alk represents alkyl with 1 to 4 carbon atoms and q represents 0, 1 or 2, m represents 1 or 2, and p represents 1 or 2.

4. Plant growth regulant composition as claimed in claim 1 comprising as active ingredient at least one compound of the formula

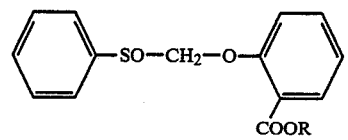

in which

R represents hydrogen, a sodium or potassium cation, one equivalent of a magnesium or calcium cation, alkyl with 1 to 8 carbon atoms, alkenyl with 2 to 8 carbon atoms, alkoxyalkyl with 1 to 4 carbon atoms in the alkoxy group and 1 to 4 carbon atoms in the alkyl part, alkylthioalkyl with 1 to 4 carbon atoms in the alkylthio group and 1 to 4 carbon atoms in the alkyl part, or the radical of the formula —CH$_2$—O—(CH$_2$—CH$_2$—O)$_q$—Alk, wherein Alk represents alkyl with 1 to 4 carbon atoms and q represents 0, 1 or 2.

5. A plant growth regulant composition according to claim 1 wherein said phenoxymethane derivative is one wherein p is 1.

6. A plant growth regulant composition according to claim 5 wherein $R_4$ is hydrogen.

7. A plant growth regulant composition according to claim 5 wherein $R_3$ is a —COOR group in ortho position wherein R is hydrogen, an alkali metal cation, one equivalent of an alkaline earth metal cation, alkyl, alkenyl, alkoxyalkyl or alkylthioalkyl.

8. A plant growth regulant composition according to claim 7 wherein R is alkyl.

9. A plant growth regulant composition according to claim 8 wherein R is methyl.

10. Method of regulating the growth of plants which method comprises applying to the plants or to their habitat a plant growth regulating effective amount of a phenoxymethane derivative of the formula

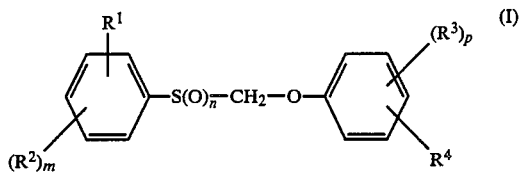

in which
- $R^1$ represnts hydrogen, alkyl, alkoxy, halogenoalkyl, halogenoalkoxy, halogen, alkoxycarbonyl, cycloalkoxycarbonyl or nitro,
- $R^2$ represents hydrogen, alkyl or halogen,
- $R^3$ represents hydrogen, alkyl, alkenyl, alkinyl, phenyl which is optionally substituted by alkyl and/or halogen, phenylalkyl which is optionally substituted by alkyl and/or halogen, alkoxy, phenoxy, halogenoalkyl, halogenoalkoxy, alkylthio, halogenoalkylthio, alkylsulphonyl, phenylthio, phenylsulphonyl, nitro, or halogen,
- $R^4$ represents hydrogen, alkyl, halogen, cycloalkoxycarbonyl, aminocarbonyl, alkylaminocarbonyl, dialkylaminocarbonyl, cycloalkylaminocarbonyl, dicycloalkyl-aminocarbonyl, phenoxycarbonyl which is optionally substituted by halogen and/or alkyl, cyano or the radical of the formula —COOR, wherein
- R represents hydrogen, an alkali metal cation, one equivalent of an alkaline earth metal cation, alkyl, alkenyl, alkoxyalkyl, alkylthioalkyl or the radical of the formula $-CH_2-O-(CH_2-CH_2-O)_q-Alk$ wherein
- Alk represents alkyl and
- q represents 0, 1 or 2,
- m represents 1, 2 or 3,
- n represents 0, 1 or 2 and
- p represents 1, 2 or 3.

11. Method as claimed in claim 10 wherein the compound of the formula (I) is applied to an area of plant cultivation in the amount of 0.01 to 50 kg per hectare.

12. Method as claimed in claim 10 wherein the compound of the formula (I) is applied to an area of plant cultivation in the amount of 0.05 to 10 kg per hectare.

13. Method as claimed in claim 10 wherein the active ingredient is selected from the compounds of the formulae

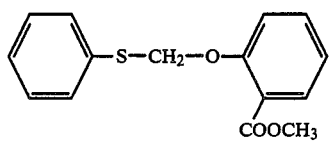

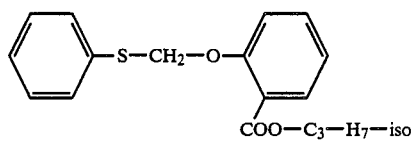

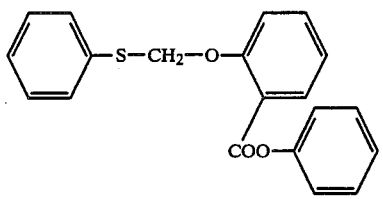

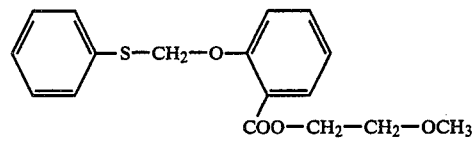

and

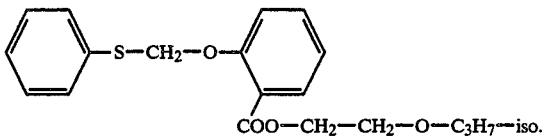

14. A method according to claim 10 wherein
- $R^1$ represents hydrogen, alkyl, alkoxy, halogenoalkyl, halogenoalkoxy, alkoxycarbonyl, cycloalkoxycarbonyl,
- $R^2$ represents hydrogen or alkyl,
- $R^3$ represents hydrogen, alkyl, alkenyl, alkinyl, phenyl which is optionally substituted by alkyl and/or halogen, phenylalkyl which is optionally substituted by alkyl and/or halogen, alkoxy, phenoxy, halogenoalkyl, halogenoalkoxy, alkylthio, halogenoalkylthio, alkylsulphonyl, phenylthio, phenylsulphonyl or nitro,
- $R^4$ represents hydrogen, alkyl, cycloalkoxycarbonyl, aminocarbonyl, alkylaminocarbonyl, dialkylaminocarbonyl, cycloalkylaminocarbonyl, dicycloalkyl-aminocarbonyl, phenoxycarbonyl which is optionally substituted by halogen and/or alkyl, cyano or the radical of the formula —COOR.

15. A method according to claim 10 wherein said plant is soya bean.

16. A method according to claim 10 wherein said plant is barley.

17. A method according to claim 10 wherein said plant is cotton.

18. A method according to claim 10 wherein said plant is sugar beet.

19. Phenoxymethane derivative of the formula

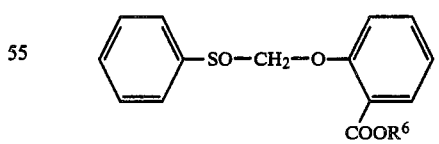

in which
- $R^6$ represents hydrogen, an alkali metal cation, one equivalent of an alkaline earth metal cation, alkyl with more than 1 carbon atom, alkenyl, alkoxyalkyl, alkylthioalkyl or the radical of the formula $-CH_2-O-(CH_2-CH_2-O)_q-Alk$ wherein
- Alk represents alkyl and
- q represents 0, 1 or 2.

20. A phenoxymethane derivative according to claim 19 wherein R is alkyl.

21. A phenoxymethane derivative according to claim 20 wherein R is methyl.

22. Plant growth regulant composition comprising as an active ingredient a plant growth regulating effective amount of at least one phenoxymethane derivative of the formula

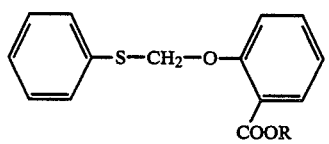

in which
R is

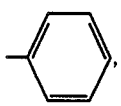

—CH$_2$—CH$_2$—OCH$_3$ or —CH$_2$—CH$_2$—O—C$_3$H$_7$—iso.

23. Plant growth regulant composition as claimed in claim 22 comprising as active ingredient the compound of the formula

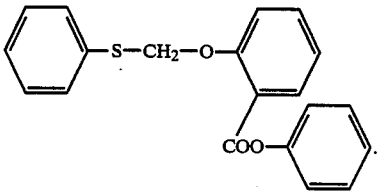

24. Plant growth regulant composition as claimed in claim 23 comprising as active ingredient the compound of the formula

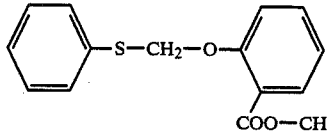

25. Plant growth regulant composition as claimed in claim 22 comprising as active ingredient the compound of the formula

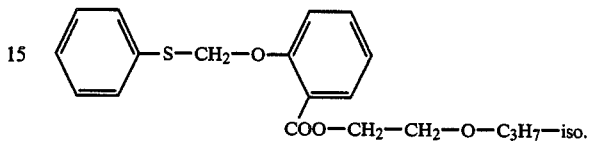

26. Phenoxymethane derivative of the formula

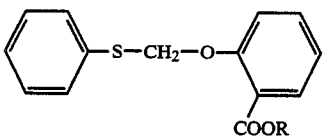

in which R is —CH$_2$—CH$_2$—O—CH$_3$ or —CH$_2$—CH$_2$—O—C$_3$H$_7$-iso.

27. Phenoxymethane derivative as claimed in claim 26, characterized by the formula

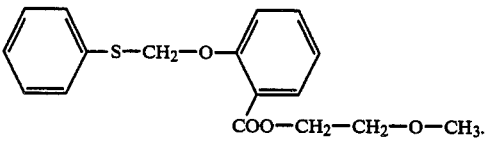

28. Phenoxymethane derivative as claimed in claim 26, characterized by the formula

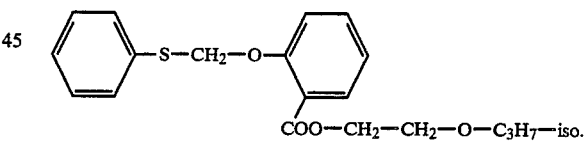

* * * * *